United States Patent [19]
Webb et al.

[11] Patent Number: 5,898,069
[45] Date of Patent: Apr. 27, 1999

[54] PHOSPHATE ASSAY

[75] Inventors: Martin Ronald Webb, St. Albans; Martin Hermann Brune, London; John Edgar Thomas Corrie, Herts, all of United Kingdom

[73] Assignee: Medical Research Council, London, United Kingdom

[21] Appl. No.: 08/581,584

[22] PCT Filed: Jul. 15, 1994

[86] PCT No.: PCT/GB94/01533

§ 371 Date: Apr. 24, 1996

§ 102(e) Date: Apr. 24, 1996

[87] PCT Pub. No.: WO95/02825

PCT Pub. Date: Jan. 26, 1995

[30] Foreign Application Priority Data

Jul. 16, 1993 [GB] United Kingdom .................... 9314792
Dec. 10, 1993 [GB] United Kingdom .................... 9325272

[51] Int. Cl.⁶ ..................................................... C12Q 1/48
[52] U.S. Cl. ......................................... 530/388.9; 530/415
[58] Field of Search ................................. 530/352, 388.9, 530/415

[56] References Cited

PUBLICATIONS

Richieri et al., "A Fluorescently Labeled Intestinal Fatty Acid Binding Protein", J. Biol. Chem., vol. 267, No. 33, pp. 23495–23501, Nov. 25, 1992.
Morita, Biosis #84;169742 (ABS only), 1983.
Richieri, Biosis #93:70384 (ABS only), 1992.
Bakin, Caplus #1988:565902 (ABS only), 1988.
Nag, Caplus #1990:548234 (ABS only), 1990.

*Primary Examiner*—Cecilia J. Tsang
*Assistant Examiner*—Patrick R. Delaney
*Attorney, Agent, or Firm*—Vincent M. Powers; Dehlinger & Associates

[57] ABSTRACT

Disclosed is a method for measuring or detecting inorganic phosphate ion in a sample. In the method, a sample is reacted with a phosphate-binding protein containing (i) an inorganic phosphate ion binding site and (ii) a detectable label that produces a signal whose amplitude changes detectably upon the binding of inorganic phosphate ion to the binding site, under conditions effective to allow binding of phosphate in the sample to the binding site. From a change in signal, the level of inorganic phosphate ion is measured or detected. Also disclosed are phosphate binding proteins for use in the method.

12 Claims, 11 Drawing Sheets

PHOSPHATE ASSAY

This application is a 371 of PCT/GB94/01533, filed Jul. 15, 1994.

The present invention relates to the detection and quantification of inorganic phosphate, especially in biological solutions. More particularly, the present invention relates to a modified phosphate binding protein and the use of such a protein in a phosphate assay.

In biological systems, changes in phosphorylation state and fluctuations in the concentration of inorganic phosphate are associated with a large number of important events. For example, a number of diseases and conditions present with elevated or depressed levels of serum inorganic phosphate concentration. Moreover, the major energy requirements of the body are fulfilled by deriving energy from alterations in the phosphorylation state of nucleotides.

Because inorganic phosphate ($P_i$) is involved in a large number of important biological processes, it is desirable to be able to measure the concentration of Pi and the changes in such concentration in biological systems Phosphate assays, which measure Pi concentration, are useful in a number of diagnostic methods, as well as in research into the functioning of biological systems.

To date, two classes of phosphate assay have been described. These are enzymatic inorganic phosphate assays and chemical inorganic phosphate assays. See, for example, Lindberg and Ernster, 1956, and Veldhoven and Mannaerts, 1987.

Enzymatic phosphate assays, for example as described in European Patent Application 0 159 513, are based on a phosphate-requiring enzyme, often a phosphorylase. In the method described in EP 0 159 513, a purine-nucleoside phosphorylase in used to convert a nucleoside (inosine) to ribose-1-phosphate and a base, in this case hypoxanthine. Hypoxanthine is then converted into a coloured agent, from which the extent of inosine conversion, which is dependent upon $P_i$ concentration, may be determined.

Another assay based on a purine nucleoside phosphorylase is described in Webb, 1992a.

Enzymatic phosphate assays tend to be relatively insensitive For example, the method described by Webb may not be used below concentrations of 2 micromolar $P_i$. Furthermore, although more rapid than chemical phosphate assays, enzymatic phosphate assays remain too slow to allow study of the kinetics of many biological systems.

Chemical phosphate assays, for example as described by Veldhoven and Mannaerts (1987), rely on the chemical generation of colour upon exposure to phosphate. For example, many chemical methods are based on the complex formation of phosphomolybdate at low pH with basic dyes, which causes a shift in absorption maxima of these dyes. The colour change is measured by spectrophotometry.

Chemical methods have the disadvantage of being extremely slow, although great sensitivity may be achieved. For example, the method of Veldhoven and Mannaerts is claimed to be sensitive to 1.5 micromolar $P_i$, to detect picomole quantities of $P_i$.

The universality of phosphate in biological systems, and the extremely high incidence of phosphate contamination in laboratory solutions makes the development of phosphate assays sensitive beyond the micromolar range of concentrations relatively unimportant. However, it remains desirable to be able to produce phosphate assays having an extremely rapid response rate, in order to monitor the kinetics of biological and chemical processes which involve the production or consumption of $P_i$.

A number of proteins are known which specifically bind to $P_i$. For example, transport of $P_i$ into and out of cells and organelles is executed by specific transport proteins. In bacterial cells, it is achieved by way of a high affinity transport system dependent on a phosphate-binding protein. Such proteins are able to specifically recognise inorganic phosphate, bind to it and transport it across cell membranes or between cellular compartments.

An example of such a protein is the E. coli phosphate binding protein (PBP) which is encoded by the phosgene of E. coli. This protein is located in the periplasm of E. coli as part of the $P_i$ scavenging system of the bacterium, which operates under conditions of $P_i$ starvation. Hence, its binding affinity for $P_i$ is extremely high.

The phoS gene has been cloned and sequenced (Magota et al, 1984; Surin et al, 1984). Moreover, it has been determined that PBP binds $P_i$ tightly (Medveczky and Rosenberg, 1970) and the crystal structure of the $P_i$-bound form has been solved to high resolution (Luecke and Quiocho, 1990). These studies have shown PBP to consist of a monomeric protein of 35 kD separated into two domains, with a $P_i$-binding cleft between them. It is postulated that the $P_i$-binding cleft moves between open and closed positions on $P_i$ binding and release.

Although this protein is extremely sensitive to $P_i$, it is not known to give rise to any rapidly detectable event upon $P_i$ binding. Accordingly, PBP has not been exploited in phosphate binding assays.

Further examples of $P_i$ transport proteins are reviewed by Torriani (1990).

A second class of $P_i$-binding protein comprises various membrane proteins which are also involved in Pi transport An example of such a protein is the Brush Border membrane protein (Kessler et al, 1986).

A third class of $P_i$-binding proteins includes $P_i$-binding enzymes. Although many enzymes bind $P_i$ weakly, some are known to bind $P_i$ strongly. Although $P_i$-binding enzymes have been used in $P_i$ assays, as indicated above, the methods used are characterised by a response too slow to allow the study of the kinetics of many biological systems.

In the present invention, it has been shown that modification of phosphate binding protein in order to attach thereto a luminescent label results in a modified phosphate binding protein which is highly sensitive to $P_i$ and produces an extremely rapid shift in luminescence characteristics when $P_i$ is bound. The modified protein may be used in an extremely rapid phosphate assay which is capable of following the kinetics of biological reactions involving phosphate, as well as in conventional $P_i$ assays such as clinical assays and in pollution testing.

According to a first aspect of the present invention, therefore, there is provided a modified phosphate binding protein comprising at least one detectable label.

The phosphate binding protein is modified in order to comprise a detectable label whose detectable characteristics alter upon a change in protein conformation which occurs on $P_i$ binding The change in the detectable characteristics is due to an alteration in the environment of the label, which is bound to the phosphate binding protein.

Preferably, therefore, the label is bound to a region of the phosphate binding protein which undergoes conformational change when $P_i$ binds. However, it is to be understood that an alteration in the environment of the label, which may result from a conformational change in a region of the protein to which the label is not directly bound, is responsible for the alteration in the luminescent characteristics of the label.

The phosphate binding protein modified in the invention may be any phosphate binding protein, but especially phosphate binding proteins involved in active transport systems which transfer $P_i$ into and out of cells and cellular compartments.

Especially preferred is the *E. coli* phos phosphate binding protein. Preferably, the label is attached in the vicinity of the binding cleft of the *E. coli* PBP, which undergoes conformational change upon $P_i$ binding.

Preferably, the detectable label is a luminescent label. However, the use of other labels is envisaged. For example, electrochemical labels could be used wherein an alteration in the environment of the label will give rise to a change in the redox state thereof. Such a change may be detected using an electrode.

Furthermore, it is envisaged that spectroscopically detectable labels, for example detectable by EPR or NMR, may be used.

The label may be attached to the phosphate binding protein by any conventional means known in the art. For example, the label may be attached via amines or carboxyl residues on the protein. However, especially preferred is linkage via thiol groups on cysteine residues.

If appropriate, natural cysteine residues in the sequence of the phosphate binding protein may be used for the attachment of the label. However, where no natural cysteine residues are available for label attachment, cysteine residues may be engineered into sequence of the phosphate binding protein, preferably by site-directed mutagenesis.

Site-directed mutagenesis will be performed by methods well known in the art for this purpose. Briefly, however, the gene encoding the phosphate binding protein is isolated and sequenced, and oligonucleotide probes are constructed to alter by recombination the codon encoding the amino acid which it is desired to change into a codon encoding cysteine. The mutated gene is subsequently expressed, typically in a bacterial expression system, to produce the mutated protein.

Preferably, the label is attached to a cysteine residue on the protein via a linkage group which is thiol-reactive.

Any thiol-reactive linkage group known in the art may be used. For example, an iodoacetamide linker may be used.

Preferably, the linkage group comprises a maleimide linker.

The luminescent label may be a fluorescent label or a phosphorescent label. The use of fluorescent labels, which may be excited to fluoresce by exposure to certain wavelengths of light, is preferred.

Preferably, the fluorescent label is selected from the group consisting of acrylodan, coumarin, dansyl aziridine, dimethylaminonaphthalenesulfonamide and derivatives thereof.

Preferably, the label is based on coumarin. Especially preferred are 7-diethylamino-3-[4'-(1-maleimidyl)phenyl]-4-methylcoumarin (CPM) and N-[2-(1-maleimidyl)ethyl]7-diethylaminocoumarin-3-carboxamide (MDCC).

Using *E. coli* phos PBP, the preferred attachment site for the label is the Alanine residue at position 197 in the amino acid sequence of PBP (A197) A197 is located at position 197 numbering from the N-terminus of the mature PBP, as shown in Magota et al (1984). Preferably, therefore, A197 is converted to cysteine. Preferably, CPM or MDCC is bonded to the cysteine residue.

The detectable label preferably shows an increase in its detectable characteristics upon $P_i$ binding. Advantageously, this increase will be of the order of 50% or greater.

It is envisaged that changes in the detectable characteristics of labels may be better exploited if two labels are used, such that conformational change of the phosphate binding protein causes the labels to move with respect to each other, altering the transfer of a for example, luminescent energy. Preferably, therefore, the modified phosphate binding protein of the invention comprises more than one detectable label.

According to the second aspect of the invention, there is provided a method for detecting inorganic phosphate in a sample comprising the steps of:

(A) causing any phosphate in the sample to bind a modified phosphate binding protein comprising of at least one detectable label; and (B) detecting a change in the detectable characteristics of the label or labels and relating this change to the concentration of phosphate present.

Preferably a "phosphate mop" is used to reduce the background levels of $P_i$ and to remove $P_i$ slowly from the phosphate binding protein, thus leaving the binding site free to detect further $P_i$ which may be released into the assay system This ensures that $P_i$ binding by the phosphate binding protein is transient. Permanent binding would reduce the useful life of an assay system as eventually all the phosphate binding protein binding sites would become occupied.

Advantageously, the phosphate mop is an enzymic system. A 7-methyl guanosine and purine nucleoside phosphorylase system is preferred.

It has been observed that by employing this method, using a modified phosphate binding protein according to the invention, it is possible to follow the kinetics of biological systems due to the extremely rapid reaction time of the method.

According to a third aspect of the invention, there is provided a modified phosphate binding protein according to the invention for use in the measurement of inorganic phosphate in the diagnosis of a disease.

The invention may be used to determine inorganic phosphate in methods of diagnosis practised in vitro or in vivo in the human or animal body.

The invention is described, for the purposes of illustration only, in the following examples.

Figure 4:
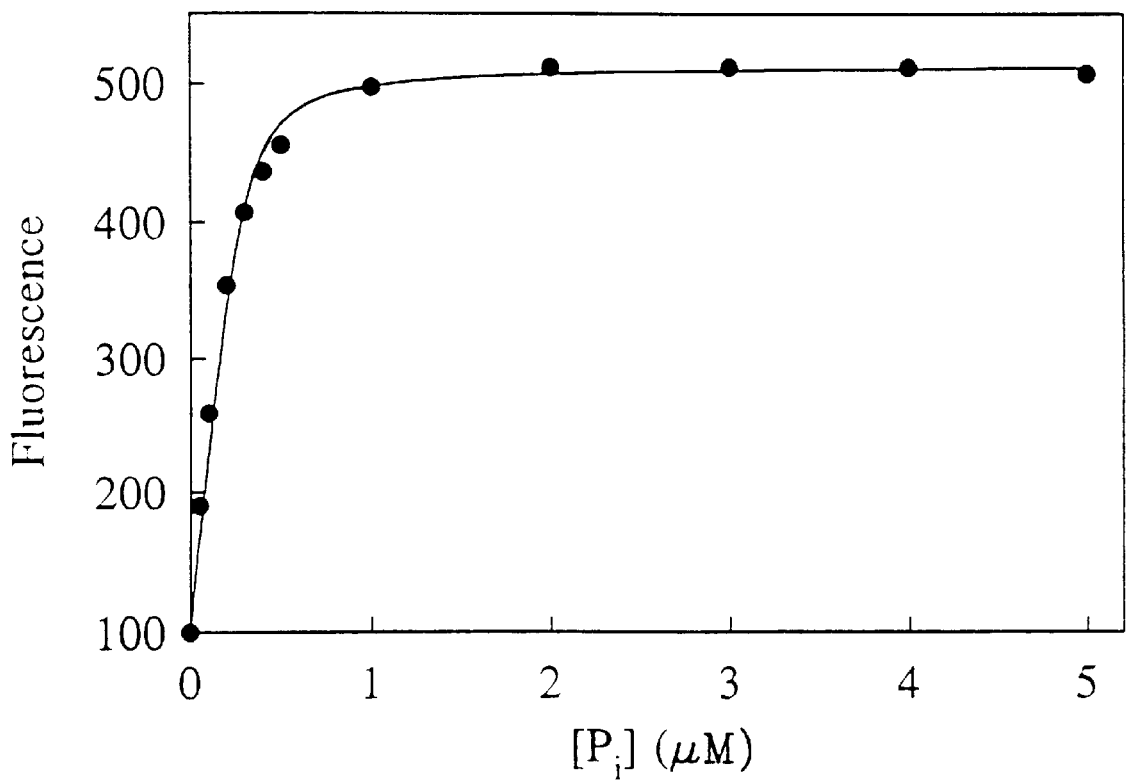

The solution at 20° C. contained 5 MM MDCC-PBP, 1 mM $MgCl_2$, 10 mM PIPES pH 7.0. Aliquots of $P_i$ were added and the fluorescence emission was measured at 465 nm with excitation at 425 nm. The data was corrected for the small amount of dilution;

FIG. 4 shows a titration of $P_i$ to MDCC-PBP to obtain the dissociation constant.

Figure 5:
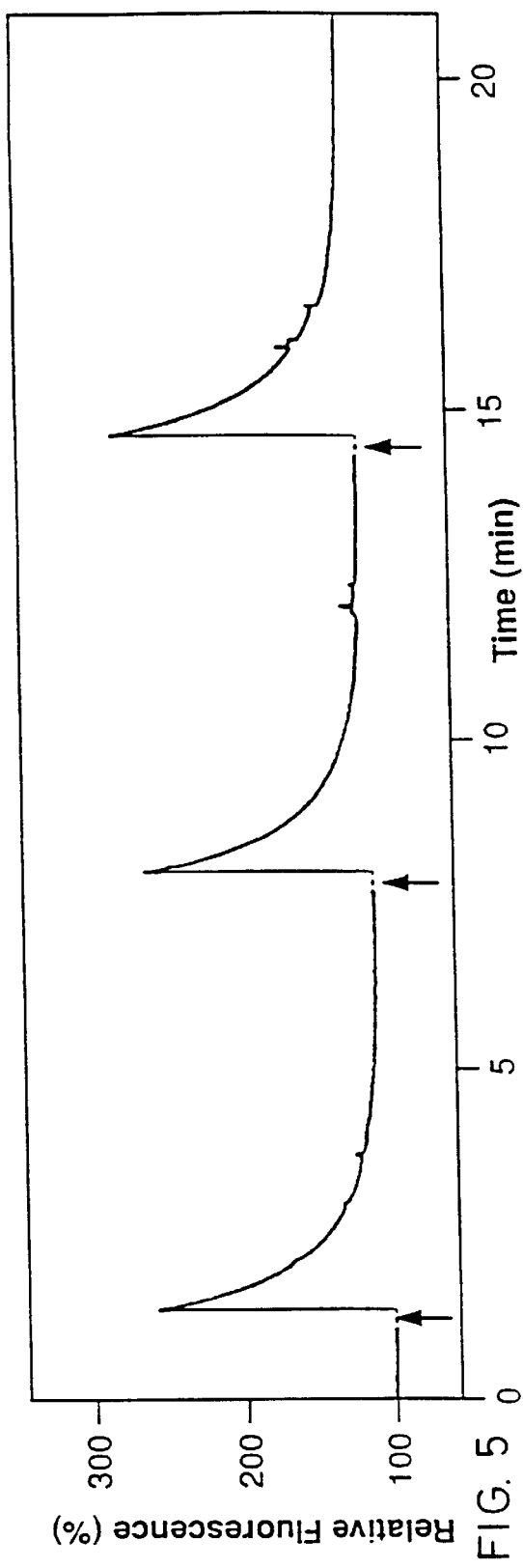

The solution at 25° C. in 10 mM PIPES, pH 7.0, 1 mM $MgCl_2$ contained 0.28 $\mu$M MDCC-PBP. Aliquots of $P_i$ were added and the fluorescence emission was measured as in FIG. 3. The data were fit to a simple binding model and the line shows the best fit, $K_d$=0.03 $\mu$M, although all values <0.1 $\mu$M fit well, and the maximum fluorescence enhancement is 415%;

FIG. 5 shows a time course of the $P_i$-induced fluorescence change using the $P_i$ mop to recover unbound MDCC-PBP.

Figure 6A:
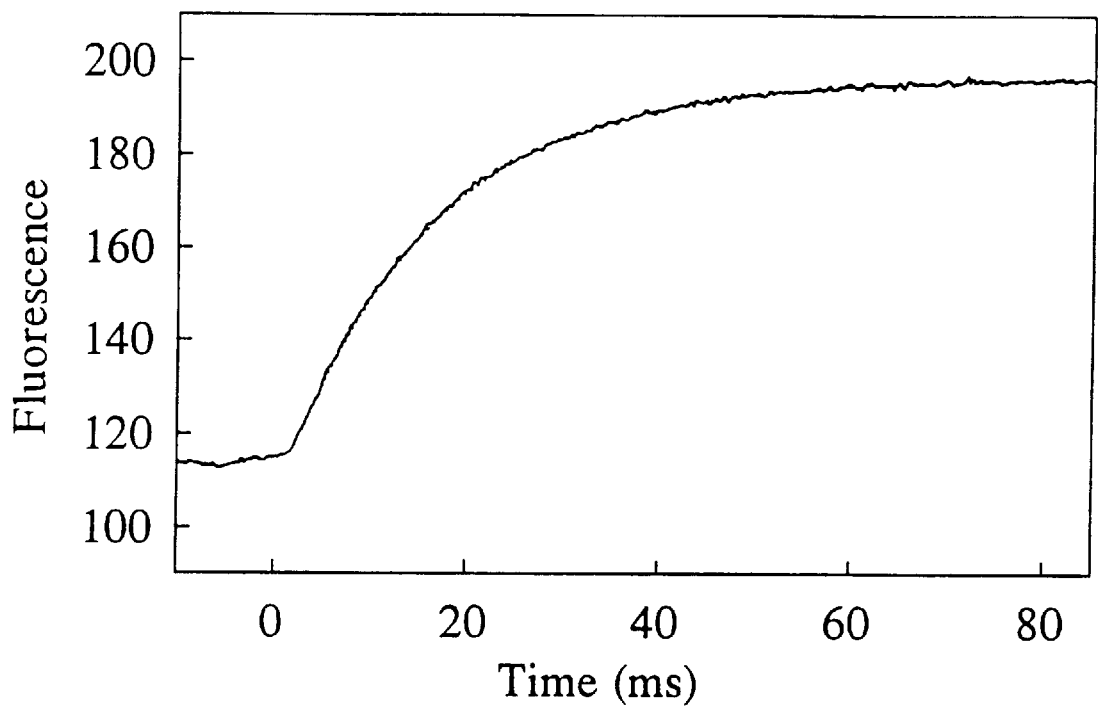
Figure 6B:
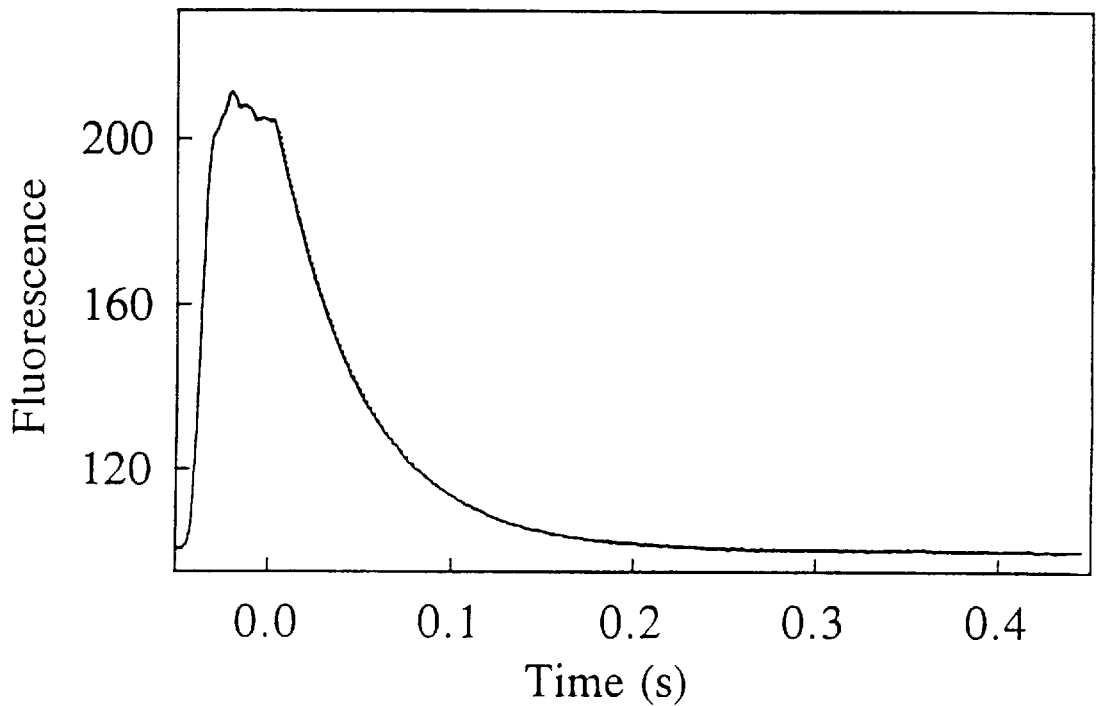

The solution contained 10 $\mu$M MDCC-PBP, 1 mM 7-methylguanosine and 0.5 unit $ml^{-1}$ purine nucleoside phosphorylase in 10 mM PIPES pH 7.0, 1 mM $MgCl_2$ at 25° C. Aliquots of $P_i$ (to 5 μM) were added as indicated by the arrows, at time intervals sufficient for the $P_i$ mop to remove $P_i$ from the MDCC-PBP and the fluorescence emission was measured as in FIG. 3;

FIGS. 6A and 6B show the kinetics of $P_i$ binding to MDCC-PBP and its release.

A. 0.1 μM MDCC-PBP (mixing chamber concentration) in 10 mM PIPES, pH 7.0 was rapidly mixed at 21° C. with different concentrations of $P_i$ in this buffer in a stopped flow apparatus, while fluorescence emission was monitored using a 455 nm cut-off filter, with excitation at 436 nm using a mercury lamp. The curve show a time course with 0.25 μM $P_i$. The signal had a time-averaging filter of <0.1×half-time. The initial lag was within the dead time of the apparatus. The best-fit single exponential (65.3 $s^{-1}$) is shown by the dashed line, almost completely hidden by the experimental curve.

Figure 7A:
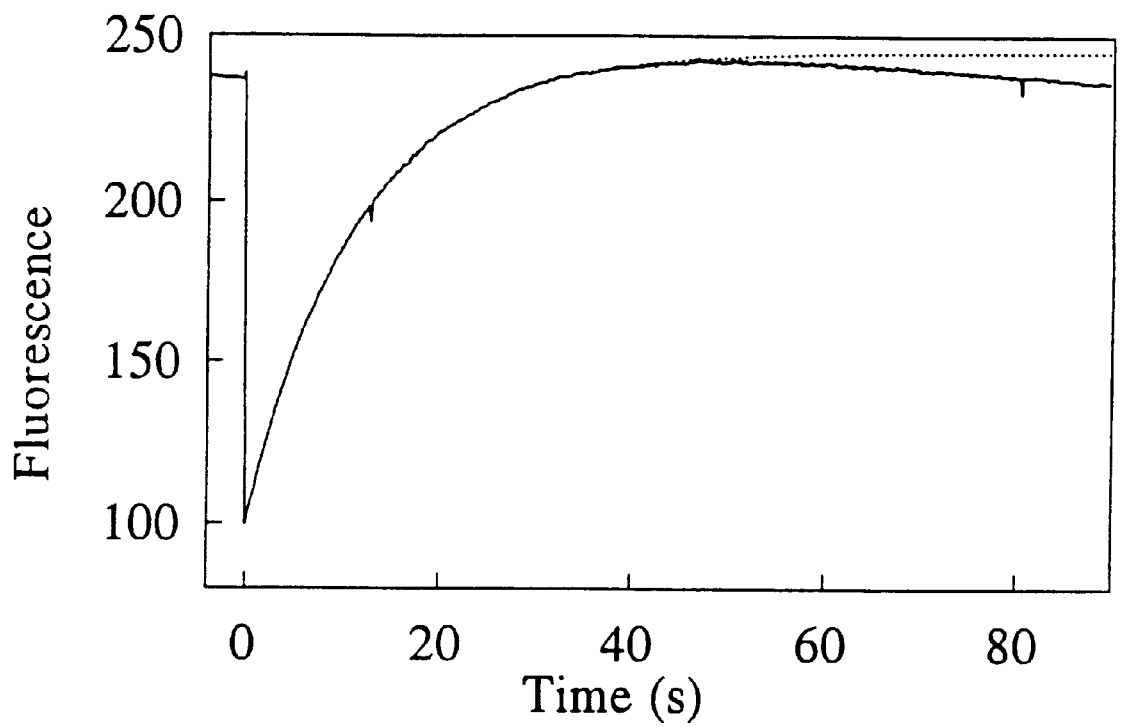
Figure 7B:
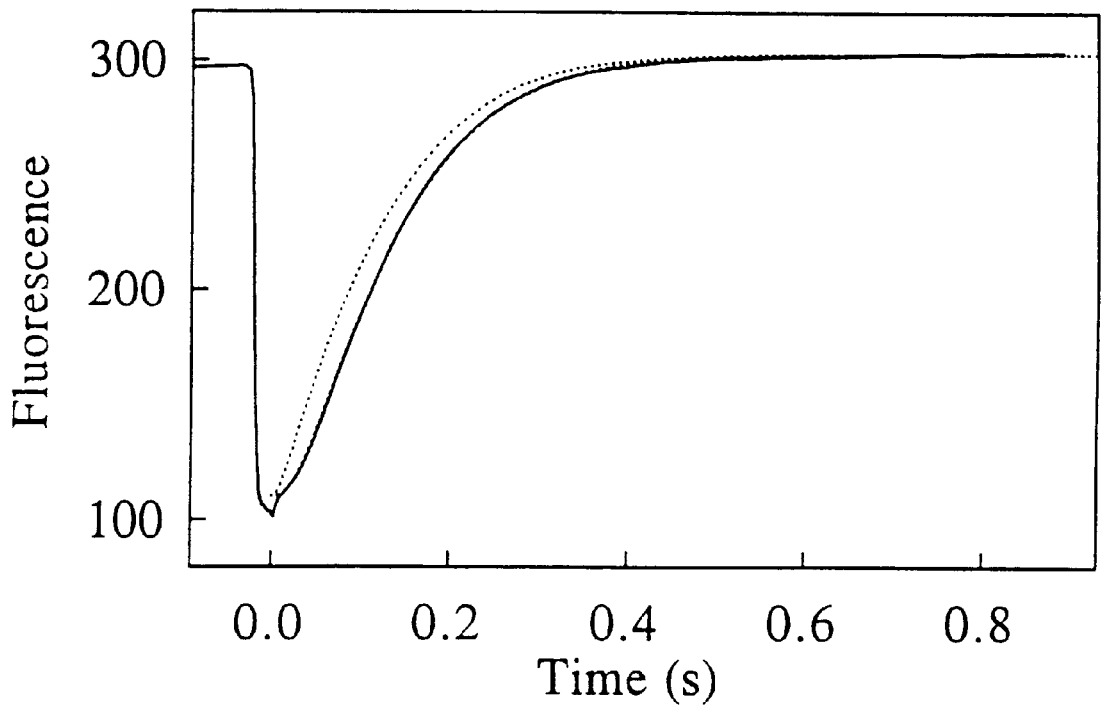

B. The release kinetics were measured by rapidly mixing 0.125 μM $P_i$, 0.25 μM MDCC-PBP with 10 μM wild-type PBP (mixing chamber concentrations) at 22° C. Other conditions were as above The best-fit single exponential (21.4 $s^{-1}$) is shown by the dashed line, almost completely hidden by the experimental curve;

FIGS. 7A and 7B show the kinetics of $P_i$ release from actomyosin subfragment 1 at low [ATP], monitored by MDCC-PBP fluorescence.

Figure 8:
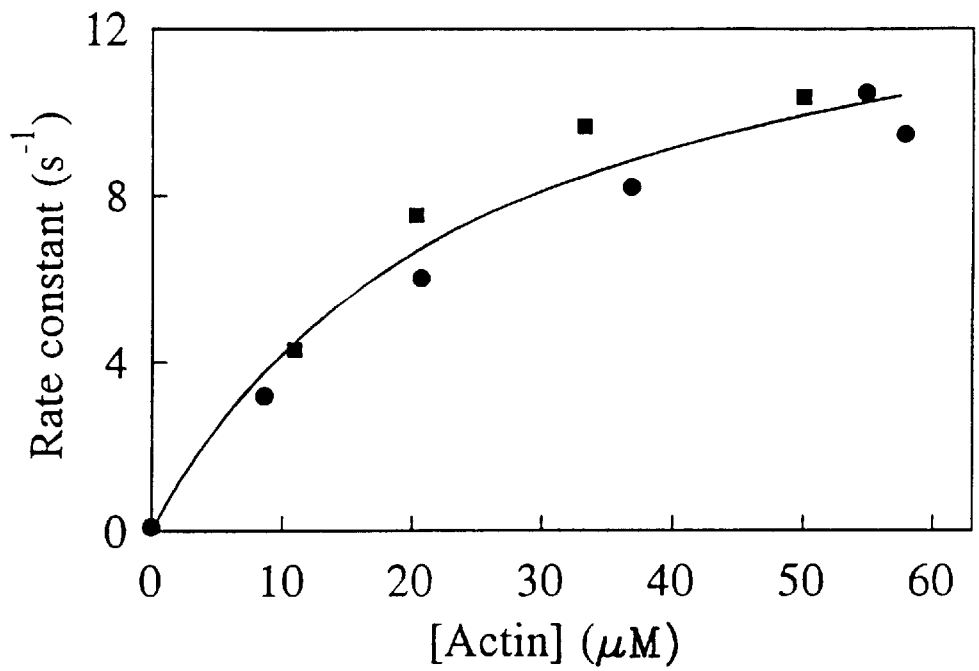

All solutions in 10 mM PIPES, 1 mM $MgCl_2$, pH 7.0 were mixed in a stopped flow apparatus and monitored as in FIG. 6. The following concentrations are those in the syringes the mixing chamber concentrations are half those quoted. A. Both syringes contained 100 μM 7-methylguanosine, 0.02 unit. $ml^{-1}$ phosphorylase. Solution 1: 16 μM myosin subfragment 1 and 18 μM MDCC-PBP. Solution 2: 5 μM ATP. The best fit exponential is also shown, k=0.0875 $s^{-1}$ (almost completely hidden by the experimental line) B. Solution 1: 18 μM MDCC-PBP, 8 μM subfragment 1, 100 μM MEG, 0.02 unit $ml^{-1}$ phosphorylase. Solution 2: 8 μM ATP, 116 μM actin, 500 μM MEG, 3 unit $ml^{-1}$ phosphorylase. The $P_i$ release predicted by the model described in the text is shown by the lower dashed line (partially hidden by the experimental line) The upper dashed line shows the theoretical total $P_i$ (bound+released) for comparison;

FIG. 8 shows the rate of actomyosin subfragment 1 ATPase as a function of actin concentration.

Figure 9:
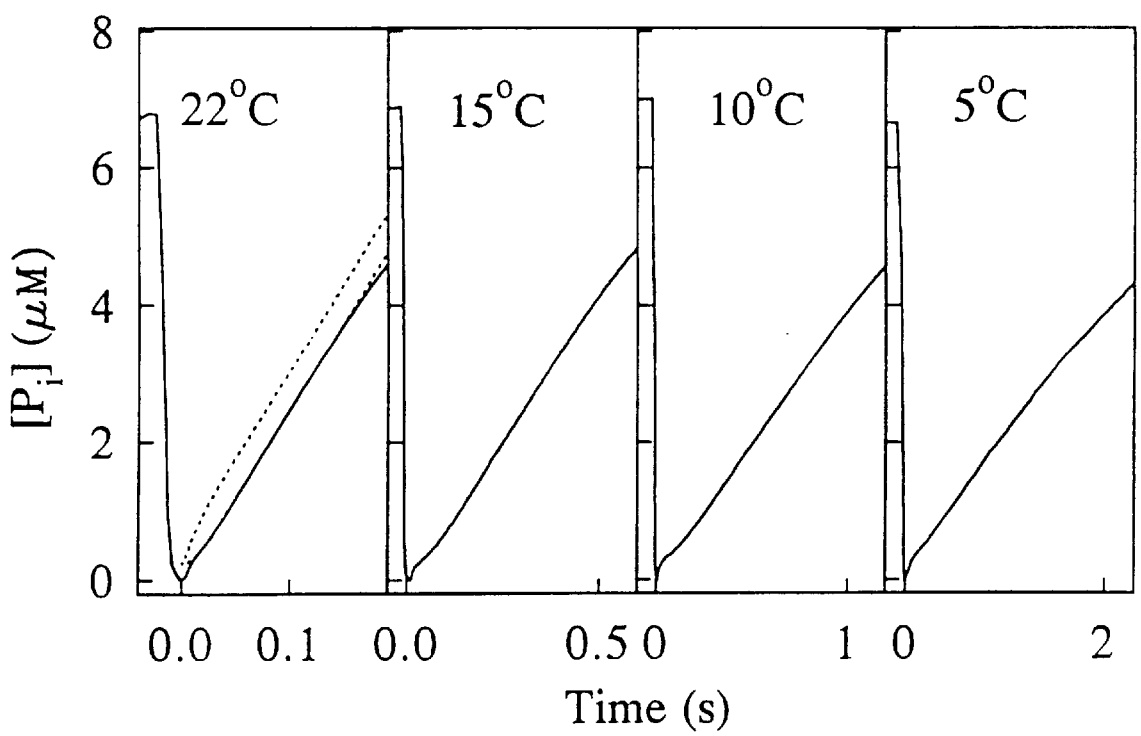

The rates are for the best fit exponentials for curves from conditions in FIG. 7: low ATP:subfragment 1 ratio. The best fit curve gives a binding constant of 26 μM and maximum exponential rate=15.2 $s^{-1}$. The circles and squares represent different sets of measurements with different protein preparations;

FIG. 9 shows the kinetics of $P_i$ release from actomyosin subfragment 1 at high [ATP], monitored by MDCC-PBP fluorescence.

Figure 12:
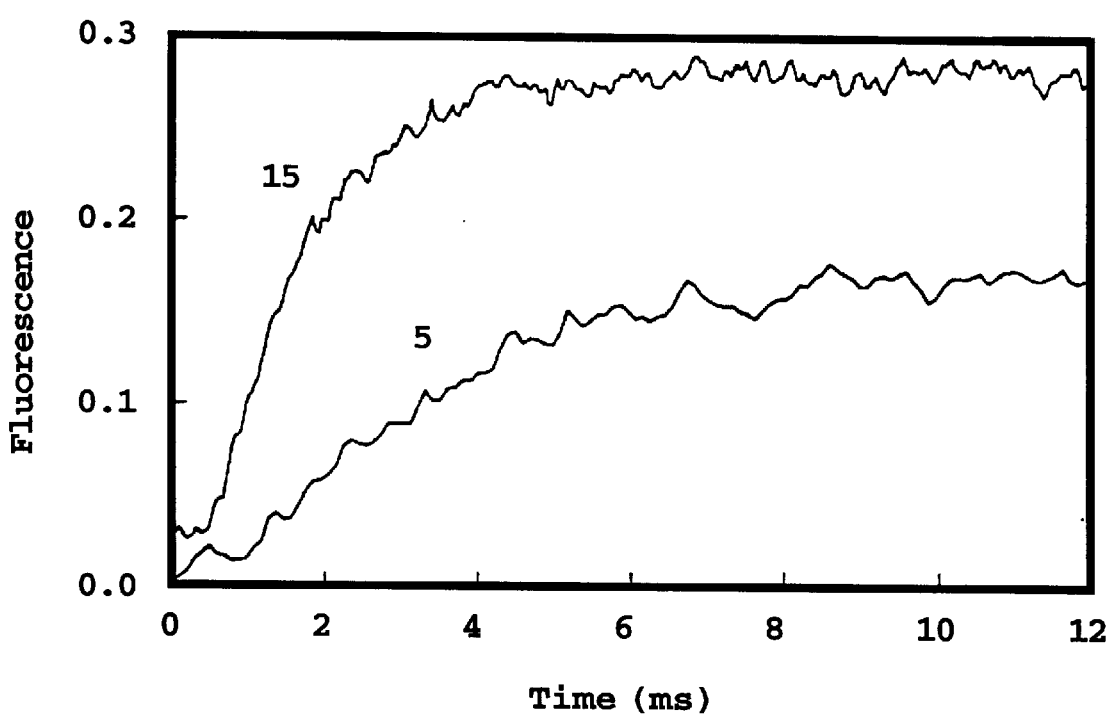
Figure 13:
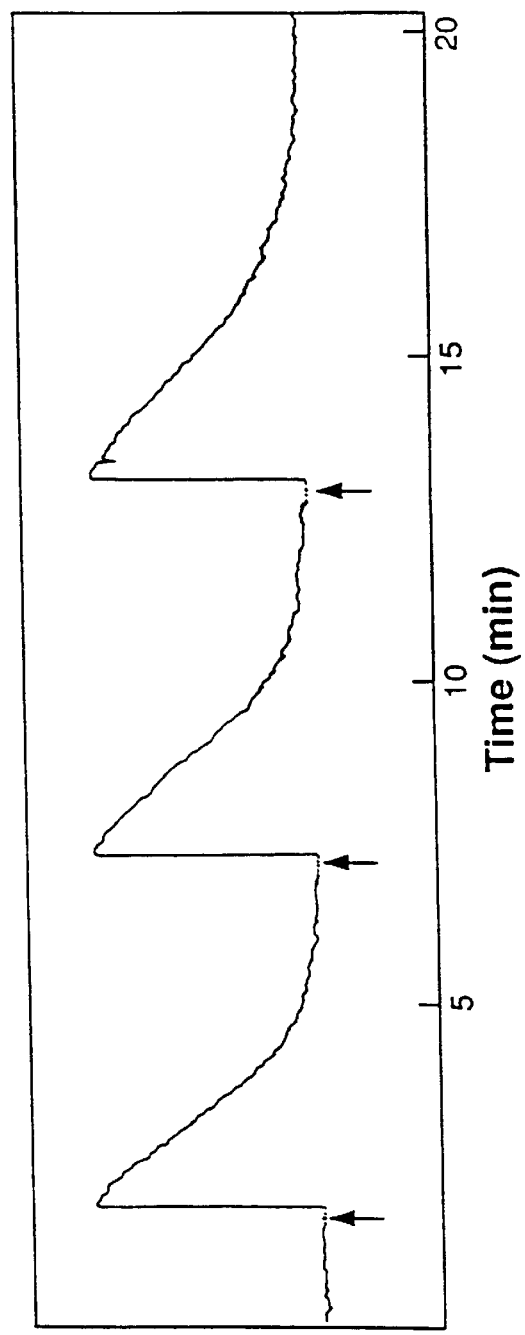
Figure 10:
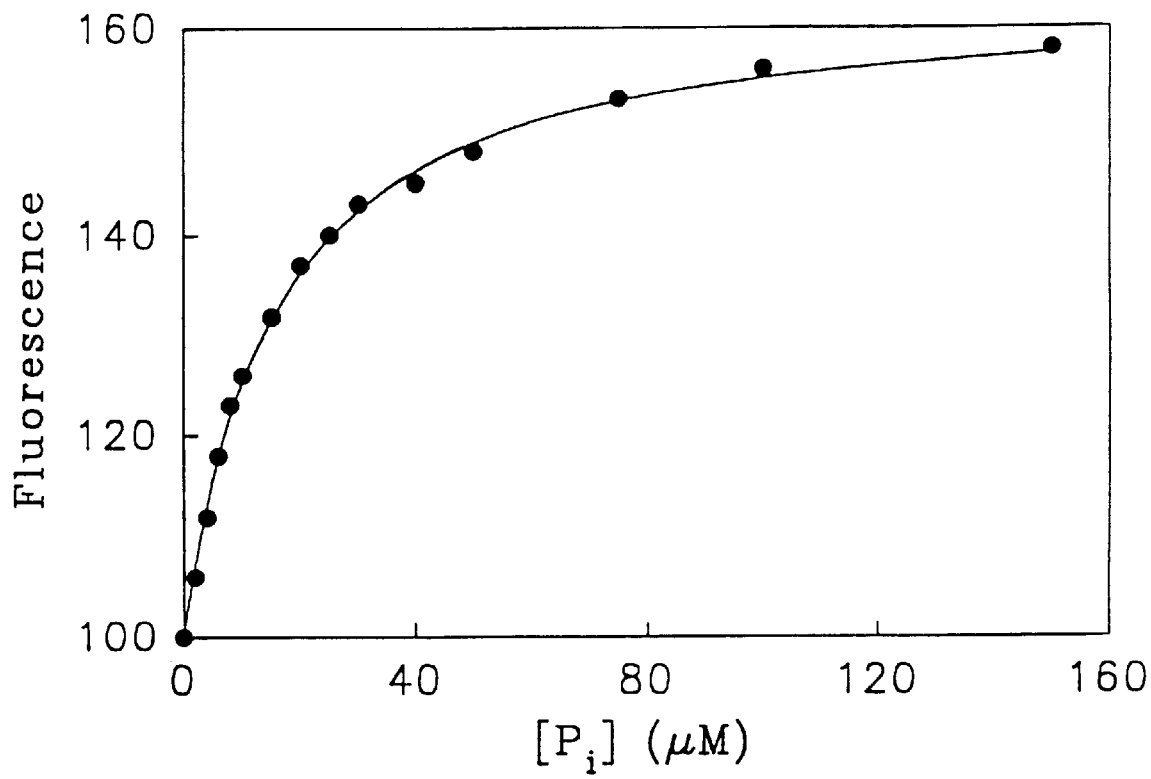
Figure 11:
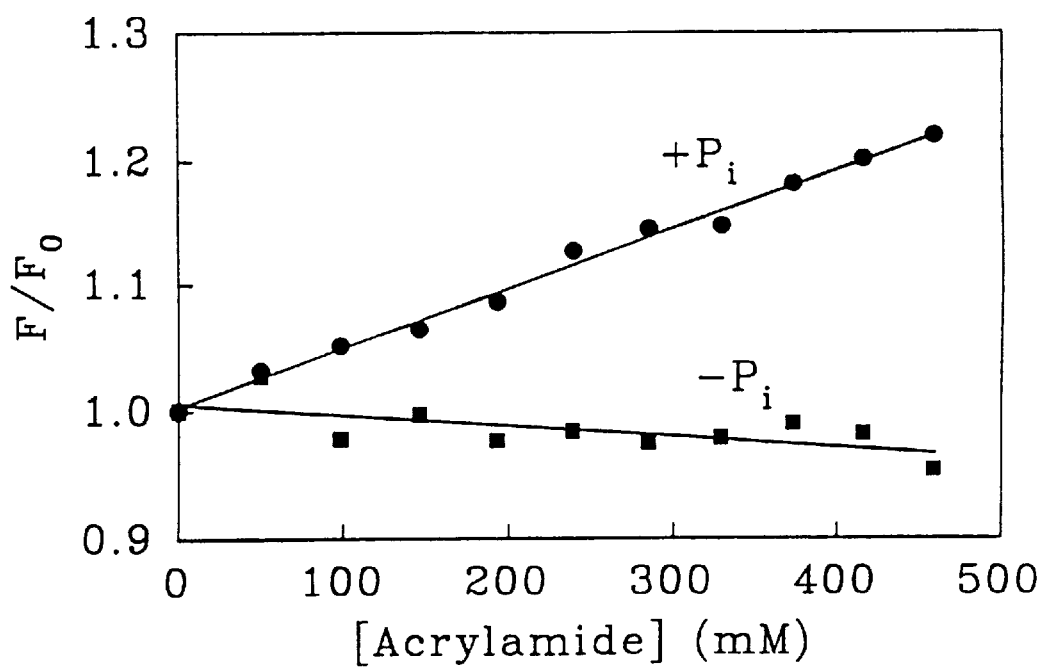
Figure 14A:
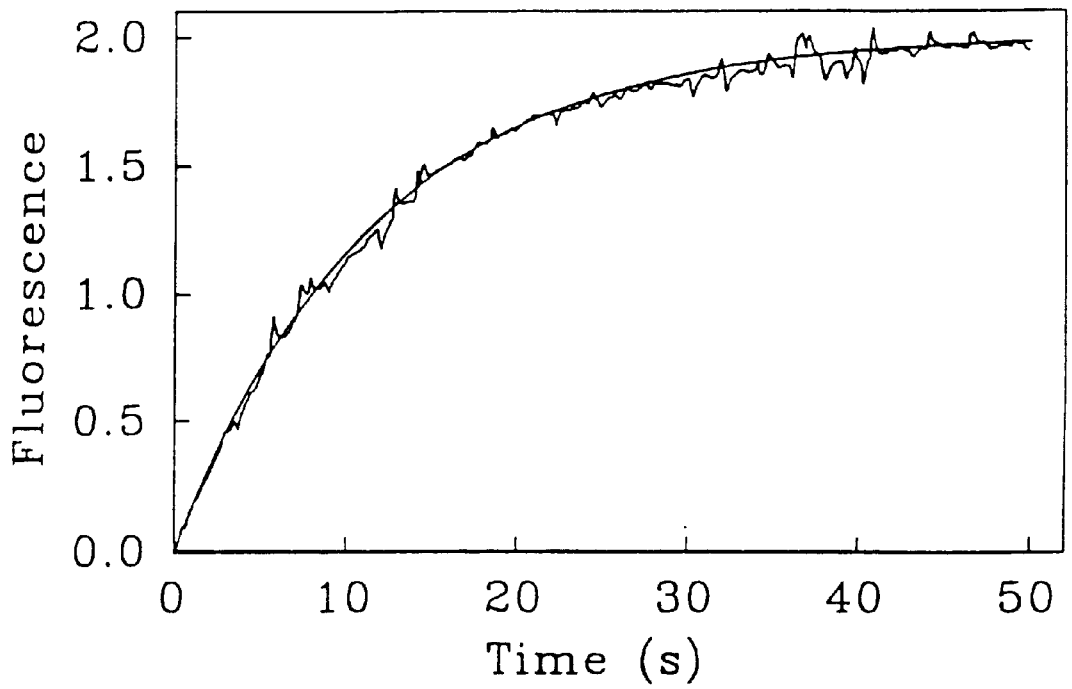
Figure 14B:
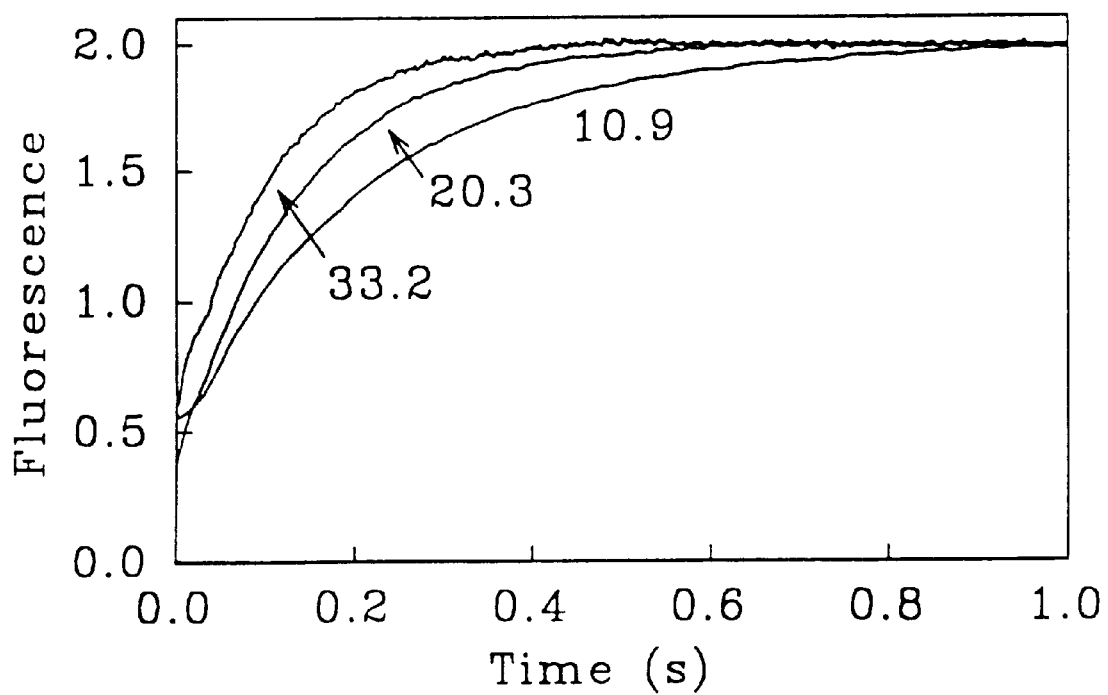
Figure 14C:
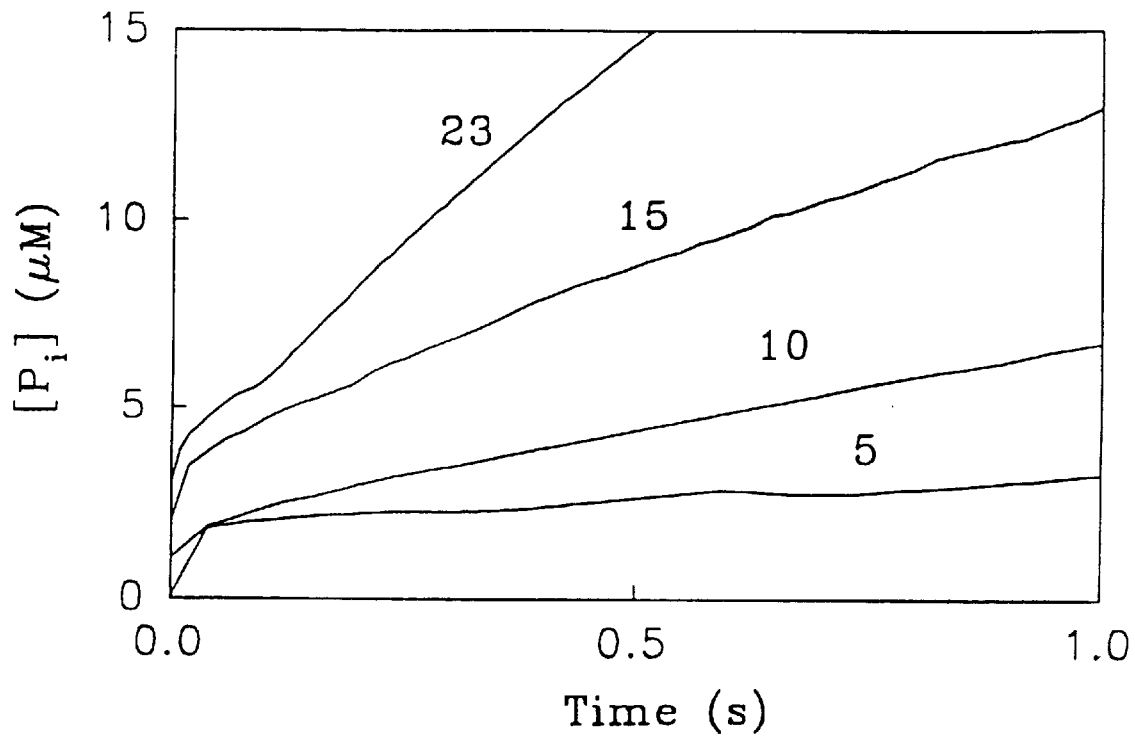
Figure 15:
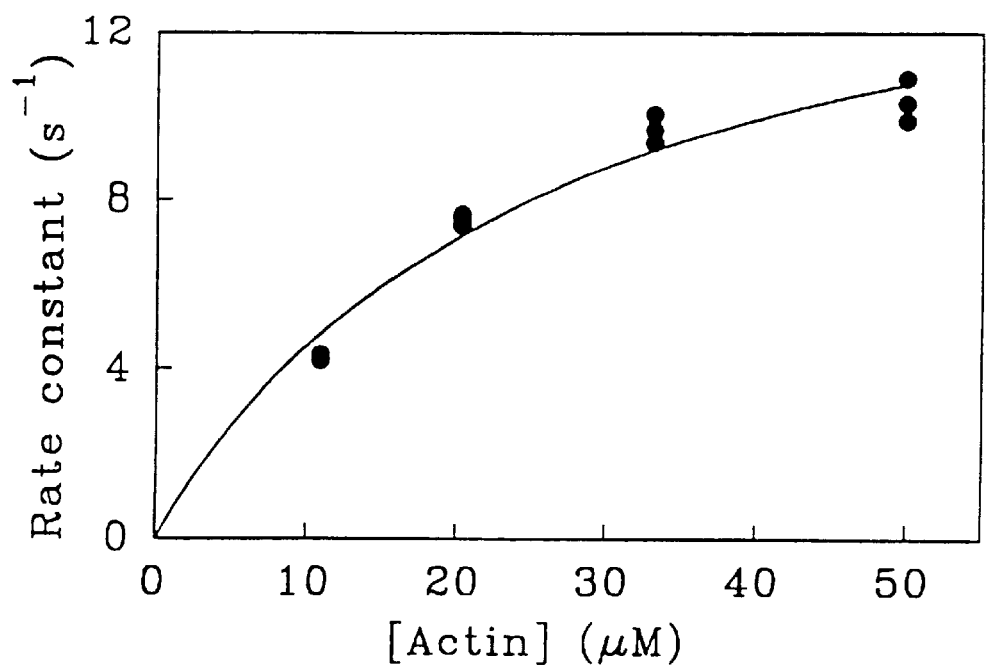
Figure 16:
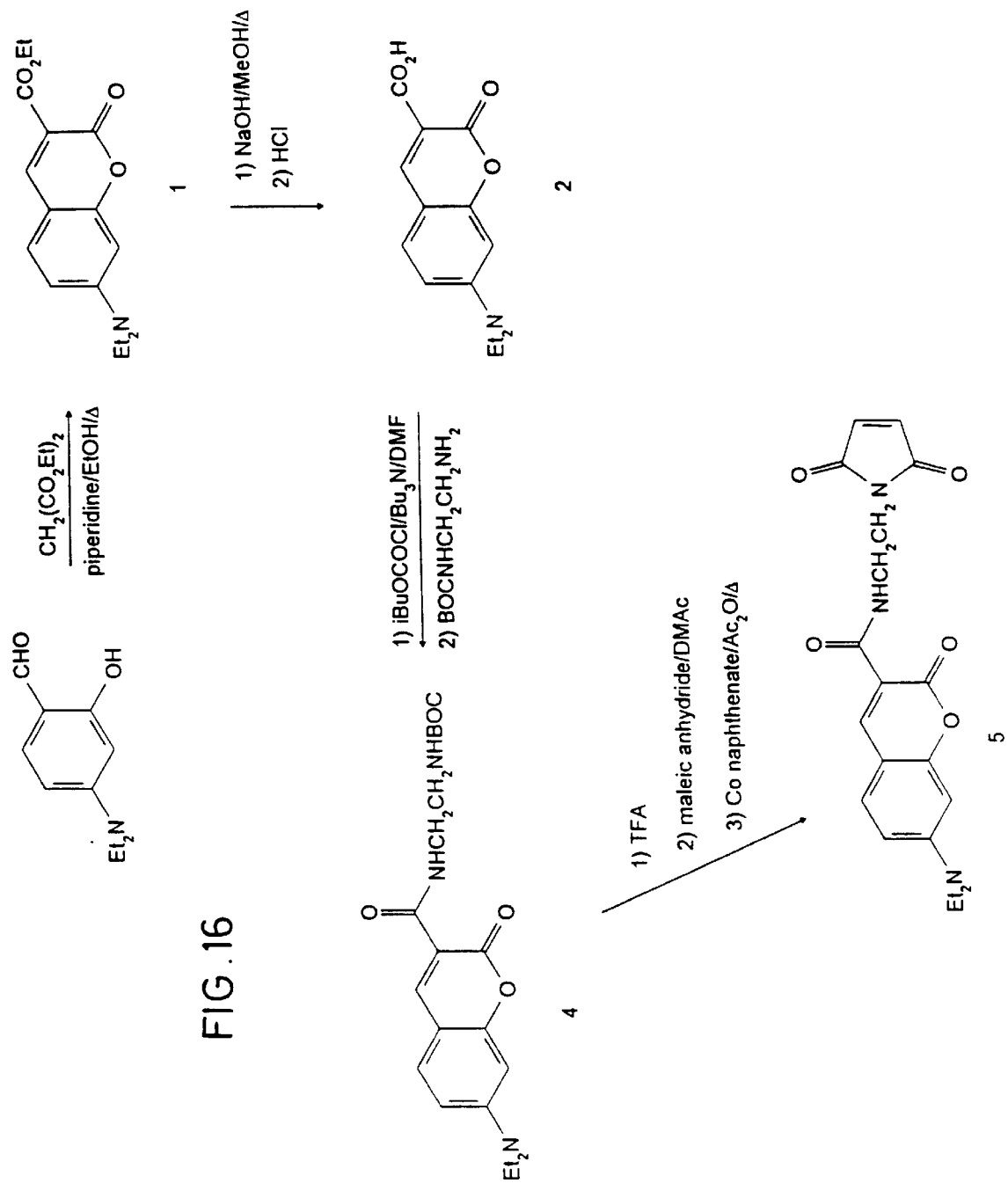

The reaction was done at various temperatures as indicated on the traces. All solutions in 10 mM PIPES, 1 mM $MgCl_2$, pH 7.0 were mixed in a stopped flow apparatus and monitored as in FIG. 6. The following concentrations are those in the syringes. For experiments at 22, 15 and 10° C.: Solution 1: 18 μM MDCC-PBP, 4 μM subfragment 1, 100 μM MEG, 0.02 unit $ml^{-1}$ phosphorylase. Solution 2: 200 μM ATP, 90 μM actin, 500 μM MEG, 0.1 unit $mL^{-1}$ phosphorylase. For the experiment at 5° C.: Solution 1: 9 μM MDCC-PBP, 4 μM subfragment 1, 100 μM MEG, 0.02 unit $ml^{-1}$ phosphorylase. Solution 2: 9 μM MDCC-PBP, 200 μM ATP, 90 μM actin, 500 μM MEG, 3 unit $ml^{-1}$ phosphorylase. The $P_i$ release at 22° C. predicted by the model described in the text, but assuming an active [subfragment 1] of 1.85 μM is shown by the lower dashed line (partially hidden by the experimental line). The upper dashed line shows the theoretical total $P_i$ for comparison;

FIG. 10 shows the tritation of $P_i$ to CPM-PBP;

FIG. 11 shows acrylamide quenching of CPM-PBP fluorescence;

FIG. 12 shows kinetics of $P_i$ binding to CPM-PBP at pH 7.0;

FIG. 13 is a time course showing $P_i$-induced fluorescence change using the $P_i$ mop to recover unbound CPM-PBP;

FIGS. 14A, 14B and 14C show the kinetics of $P_i$ release from actomyosin subfragment 1, monitored by CPM-PBP fluorescence;

FIG. 15 shows the rate of actomyosin subfragment 1 ATPase as a function of actin concentration; and FIG. 16 shows a reaction sequence for the synthesis of MDCC.

EXPERIMENTAL PROCEDURES

Bacterial strains and plasmids Escherichia coli strains TG1 (supE hsdΔ5thiΔ(lac-proAB), F'[traD36proAB+lacI_$^q$ lacZΔM15]), and JM109 (recA1 supE44 endA1 hsdR17 gvrA96 relA1 thiΔ(lac-proAB),F'[traD36 proAB+lacI_$^q$ lacZΔM15]) (Gibson, 1984; Yanisch-Perron et al. 1985) were used for single strand DNA production from phagemid pEMBL9 derivates (Dente et al. 1983) and for screening of mutated pros genes. E. coli strain ANCC75 (leu purE trp his argG rpsL pho564 metA or metB thi) and plasmid pSN5182 containing the phos gene, were provided by Dr. A. Nakata (Osaka University) and were used for overproduction of PBP (Horita et al. 1983).

Materials LB medium was prepared according to Sambrook et al (1989) For expression of phoS a minimal medium, TG plus, was used based on 120 mM Tris.HCl, pH 7.2, containing 80 mM NaCl, 20 mM KCl, 20 mM $NH_4Cl$, 3 mM $Na_2SO_4$, 100 mg.$l^{-1}$ L-arginine.HCl 50 mg.$l^{-1}$ L-leucine, 40 mg.$l^{-1}$ L-histidine.HCl, 20 mg.$l^{-1}$ L-methionine, 10 mg.$l^{-1}$ L-tryptophan, and 20 mg.$l^{-1}$ adenosine.

Myosin subfragment 1 was prepared by chymotryptic digestion of rabbit skeletal myosin as described by Weeds & Taylor (1975) and stored in liquid nitrogen at ~1 mM. Concentrations were calculated on the basis of a molecular weight of 115000 and $E^{1\%}$ (280 nm)=7.9 $cm^{-1}$. The protein was ~50% active based on the K+-ATPase activity. F-actin from rabbit skeletal muscle was prepared essentially as described by Lehrer and Kerwar (1972). Concentrations were measured from the absorbance spectra assuming $E^{1\%}$ (290 nm)−$E^{1\%}$(310 nm) =6.2 $cm^{-1}$. Purine nucleoside phosphorylase was the "bacterial" protein from Sigma and was assumed to be one third active (Webb, 1992a)

Other enzymes were from Boehringer Mannheim, New England Biolabs, and Amersham. Fluorescent labelling reagents were obtained from Molecular Probes or provided by Dr. J. Corrie (National Institute for Medical Research, London). Radiochemicals were from Amersham. All other biochemicals and chemicals were of the highest purity available.

Cloning and mutagenesis For site-directed mutagenesis the 1.4 kb EcoRI/PsI fragment of pSN5182 containing the phos gene was cloned into the multilinker site of the phagemid vector pEMBL9, yielding pEPS9 (504 kb). From this plasmid ssDNA was prepared according to Dente at al (1983) using M13K07 as a helper phage. Oligonucleotide directed site-specific mutagenesis was carried out according to the Eckstein method (Taylor at al, 1985; Hakamaye & Eckstein, 1986). Where applicable the mutation resulted in a new restriction site such that restriction digests were used for quick identification of mutated phos genes. Mutations were verified by DNA sequencing.

Expression of phoS genes from pEPS9 derivatives was low, so the gene was transferred to pSN5182. The mutated phos genes were excised from pEPS9 as 1.4 kb EcoRI/PstI fragments and ligated with the 3.6 kb EcoRI/PstI fragment of pSN5182, yielding pSN5182/N plasmids of 5.0 kb. pSN5182/N plasmids were transformed into ANCC75 cells. General cloning techniques were performed as described by Sambrook et al (1989).

Expression of phoS and purification of PBP A 2 ml overnight culture of ANCC75 containing either pSN5182 with wild type or pSN5182/N with mutated phos genes was diluted into 100 ml LB medium containing 12.5 mg.l$^{-1}$ tetracycline. After 12 h at 37° C., 10 ml of this culture were diluted into 500 ml of TG plus medium containing 0.64 mM $KH_2PO_4$, 2 g.L$^{-1}$ Glucose, 0.01 mM $FesO_4$, 0.2 mM $MgSO_4$, 0.2 Mm $CaCl_2$, and 12.5 mg.L$^{-1}$ tetracycline Cells were grown for 16–20 h, pelleted by centrifugation at 3000 rpm at room temperature for 30 min, and resuspended in 500 ml TG plus containing the same supplements except 0.064 mM $KH_2PO_4$ was used. Cells were grown for another 12–16 h and then harvested.

PBP was released from the cells' periplasm by osmotic shock (Willsky & Malamy, 1976). The final periplasmic extract was buffered with 10 mM Tris.HCl, pH 7.6 and typically had a volume of 40 ml per liter cell culture The extract was applied to a DEAE-cellulose column (2.6×28 cm), equilibrated with 10 mM Tris.HCl, pH 7.6, 1 mM $MgCl_2$. After loading, the column was washed with one volume of equilibration buffer, and then a 250 ml continuous gradient of 0–100 mM NaCl in the same buffer was applied. PBP was the major protein present and was pooled and concentrated in an Amicon pressure concentrator. The final protein solution in small aliquots was stored at –80° C.

Labelling A197C PBP with 7-diethylamino-3-[4'-(1-maleimidyl)phenyl]-4-methylcoumarin (CPM) 100 $\mu$M A197C and 400 $\mu$M CPM were incubated in 8 ml of 10 mH Tris-HCl, pH 8.1 at room temperature for 4 h on an end-over-end mixer. The protein was purified on a Biogel P4 gel filtration column (15×70 cm) eluting with 10 mM Tris.HCl pH 8.0. The protein was filtered through a 0.2$\mu$m pore size membrane filter (Acrodisc 13, Gelman), and loaded onto a 10 ml Q-Sepharose column, equilibrated with 10 mM Tris.HCl, pH 7.6, 1 mM $MgCl_2$. After washing, the protein was eluted by a 200 mL gradient of 0–50 mM NaCl in this buffer. The purity of the labelled protein was checked by its fluorescence change with $P_i$, by its absorbance spectrum and by SDS gel electrophoresis with both Coomassie blue staining and fluorescence visualisation. The yield was typically about 50% of the starting material.

Synthesis of MDCC

Figure 1A:
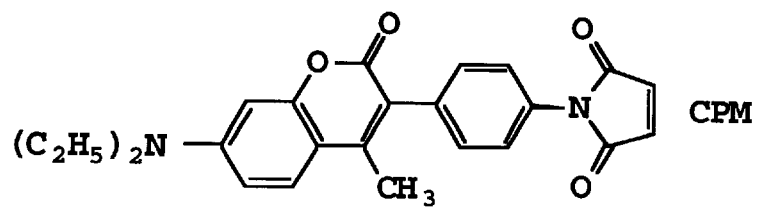
FIGS. 1A–1B shows the structures of CPM and MDCC.
Figure 1B:
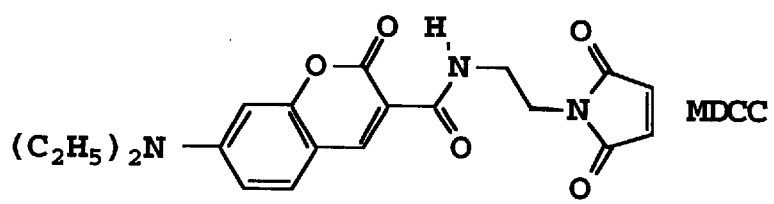

N-[2-(1-Maleimidyl)ethyl] 7-diethylaminocoumarin-3-carboxamide (MDCC) has the structure shown in FIG. 1, with CPM for comparison. The synthesis was performed as follows:

General Details—Microanalyses were carried out by MEDAC Ltd., Uxbridge, Middlesex. $^1$H NMR spectra were determined, unless otherwise stated, in $CDCl_3$ solutions on a JEOL FX90Q spectrometer with tetramethylsilane as internal reference J Values are given in Hz. Merck 9385 silica gel was used for flash chromatography. Light petroleum was the fraction boiling at 40–60° C. Organic extracts were dried over anhydrous $Na_2SO_4$. Cobalt naphthenate was from Fluka, Gillingham, Dorset. A reaction scheme is shown in FIG. 16.

Ethyl 7-diethylaminocoumarin-3-carboxylate (1).—A solution of 4-diethylamino-2-hydroxy-benzaldehyde (29.8 g, 154 mmol) and diethyl malonate (23.8 ml, 157 mmol) in ethanol (185 ml) was treated with piperidine (1.37 ml, 13.9 mmol) and heated under reflux for 4 h. The solution was allowed to cools then concentrated under reduced pressure to approx. half-volume diluted with ether and washed with water, dilute aq. NaOH and water, dried and evaporated under reduced pressure. Trituration of the residue with EtOH (approx. 15 ml) gave yellow crystals which were recrystallised from EtOAc-light petroleum to give the ester 1 as bright yellow prisms (18 the m.p. 76–77° C. A sample recrystallised a second time had m.p. 77–78° C. (Found: C, 66.4; H, 6.7g N, 4.8. $C_{16}H_9NO_4$ requires C, 66.4; H, 6.6; N, 4.8%). The discrepancy with the m.p. (87° C.) reported by Kendal et al. (GB 867,592), together with the sharp m.p. and satisfactory analytical result for the present sample suggests that the digits of the reported value may accidently have been transposed.

7-diethylaminocoumarin-3-carboxylic acid (2).—A solution of the ester 1 (11.6g, 40 mmol) in MeOH (100 ml) was heated under reflux and 0.5 M aq. NaOH (100 ml) was added rapidly. A yellow solid precipitated within 5 min and the mixture was cooled and acidified with 2 M aq. HCl to give an orange solid which was filtered and washed with 2 M aq. HCl, then with water until neutral and finally with MeOH (50 ml), and dried in vacuo to give the acid 2 (9.4 g) A sample recrystallised from MeOH-diisopropyl ether as orange laths, m.p. 231–232° C. (lit. m.p. 227–229° C. see U.S. Pat. No. 4,317,774).

t-Butyl N-(2-aminoethyl)carbamate (3).—Benzyl N-(2-aminoethyl)carbamate was prepared by the method of Atwell and Denny (1984), and converted to t-butyl N-[2-benzyloxycarbonylamino)ethyl]carbamate, m.p. 129–130° C. (lit. m.p. 123–124° C.) as described (see Barker et al., 1981). The latter compound (1.5 g, 5.1 mmol) was dissolved in EtOH (45 ml) and 5% Pd-C (1.2 g) was added. The mixture was shaken under hydrogen at 5 atm and room temp. for 18 h and the catalyst was filtered and washed with ethanol. The combined filtrates were evaporated under reduced pressure to afford the monoamine 3 (0.8 g, 5 mmol) as a colourless oil, which was used without further purification.

N-[2-(t-Butoxycarbonylamino)ethyl] 7-diethylaminocoumarin-3-carboxamide (4).—A solution of 7-diethylaminocoumarin-3-carboxylic acid 2 (1.15 g, 5 mmol) and tri-n-butylamine (1.38 g, 7.5 mmol) in dry DMF (50 ml) was cooled in an ice bath and treated with isobutyl chloroformate (0.715 g, 5.2 mmol). The solution was stirred in the ice bath for 0.5 h, then a solution of the amine 3 (0.8 g, 5 mmol) in dry DMF (5 ml) was added. The mixture was allowed to warm to room temp. and kept for 3 h, then diluted with EtOAc and washed thoroughly with water, dilute aq. HCl, aq. $NaHCO_3$ and water, dried and evaporated. The residue gave a yellow solid after trituration with a little ether. A portion (400 mg) was purified by flash chromatography to give the amide 4 as yellow prisms (0.345 g), m.p. 157–158° C. after crystallisation from EtOAc-light petroleum The remaining material crystallised without chromatography to give a further portion of the product (0.55 g, total yield 45%) (Found. C, 62.6;. H, 7.3; N, 10.4. $C_{21}H_{29}N_3O_5$ requires C, 62.5; H, 7.2; N, 10.4%); $\delta_H$ 8.95 (1 H, t, J 5.5, NH), 8.68 (1 H, s, 4-H), 7.42 (1 H, d, $J_{ortho}$ 8.8, 5-H) , 6.64 (1 H, dd, $J_{meta}$ 2.3, 6-H), 6.49 (1 H, d, 8-H), 5.08 (1 H, br S, NH), 3.23–3.64 (8 H, m, 4×CH$_2$), 1.44 (9 H, S, CMe$_3$) and 1.24 (6 H, t, J7, 2×Me).

N-[2-(1-Maleimidyl)ethyl] 7-diethylaminocoumarin-3-carboxamide (5).—The amide 4 (0.88 g, 2.18 mmol) was dissolved in trifluoroacetic acid (10 ml) and kept at room temp. for 1 h. The solvent was evaporated under reduced pressure and the residue was partitioned with chloroform and aq. NaHCO$_3$. The chloroform layer was dried and evaporated under reduced pressure to leave a yellow foam (0.60 g). Maleic anhydride (0.196 g, 2 mmol) was added, followed by dry N,N-dimethylacetamide (2 ml) at room temp. and the mixture was warmed to 60° C. over 20 min. An aliquot (94 µl) of a solution of cobalt naphthenate (20 µl) in N,N-dimethylacetamide (1 ml) was added, followed by acetic anhydride (0.38 ml), and the solution was heated at 70–80° C. for 2 h, then cooled, diluted with water and extracted with EtOAc (see GB 2,018,253). The organic extract was washed with water, dried and evaporated under reduced pressure. The residue was purified by flash chromatography [EtOAc-light petroleum (7.3)] to give the maleimide 5, which crystallised from EtOAc-light petroleum as fine yellow needles (0.22 g, 26%), m.p. 179–181° C. (Found: C, 62.5; H, 5.5: N, 10.8. C$_{20}$H$_{21}$N$_3$O$_5$ requires C, 62.65; H, 5.5; N, 11.0%) $\lambda_{max}$ (EtOH)/nm 258 and 418 ($\epsilon$/M$^{-1}$cm$^{-1}$ 13,150 and 45,000); $\lambda_{max}$ [EtOH-50 mM Na phosphate, pH 7.0 (1:9)]/nm 264 and 430 ($\epsilon$/M$^{-1}$cm$^1$ 12,800 and 46,800); δ 8.88 (1 H, t, J 5.7, NH), 8.66 (1 H, S, 4-H); 7.41 (1 H, d, J$_{ortho}$ 8.8, 5-H), 6.69 (1 H, S, CH=CH), 6.63 (1 H, dd, J$_{meta}$ 2.7, 6-H), 6.47 (1 H, d, 8-H), 3.39–3. 88 (8 H, m, 4×CH$_2$) and 1.24 (6 H, t, J7, 2×Me).

The fluorescence spectrum was measured for a solution of maleimide 5 (1.3 µM) in 50 mM sodium phosphate, pH 7.0 before and after addition of 2 mM dithiothreitol (DTT) In both cases the excitation wavelength was set at 430 nm. In the absence of DTT the emission maximum was at 477 nm, and moved to 480 nm after addition of DTT, with an accompanying 4.25-fold increase in intensity.

Note concerning maleimide synthesis

In the procedure of GB 2,018,253, cobalt naphthenate is used to promote cyclisation of N-alkylmaleamic acids to the corresponding maleimides. While the formation of N-aryl maleimides is readily achieved by heating N-arylmaleamic acids with fused sodium acetate and acetic anhydride, N-alkyl maleimides are much less readily prepared. The procedure of Keller & Rudinger (1975), while suited to water soluble amines (see DE 3,919,915 for a recent example) has not to our knowledge been applied to amines insoluble in water. While the procedure of Keifer and Haug (GB 2,018,253) is effective for N-alkylmaleidimes as claimed in our hands it was difficult to remove coloured impurities from the product. By using 120fold less cobalt naphthenate than that specified, the yield of maleimide was not greatly diminished, but the purification of the product was greatly facilitated.

Labelling A197C PBP with N-[2-(1-maleimidyl)ethyl]-7-diethylaminocoumarin-3-carboxamide (MDCC) 100 µM A197C and 500 µM MDCC (from a 25 mM solution in dimethylformamaide) were incubated in 8 ml of 20 mM Tris-HCl, pH 8.1 at room temperature for 4 h on an end-over-end mixer. The protein was filtered through a 0.2 µm pore size membrane filter (Acrodisc 13, Gelman) and purified on a Biogel P4 gel filtration column (1.5×70 cm) eluting with mM Tris-HCl, pH 8.0. The protein was loaded onto a 25 ml Q-Sepharose column, equilibrated with 10 mM Tris-HCl, pH 7.6, 1 mM MgCl$_2$. After washing, the protein was eluted by a 200 mL gradient of 0–50 mM NaCl in this buffers. The purity of the labeled protein was checked by its fluorescence change with P$_i$, by its absorbance spectrum and by SDS gel electrophoresis with both Coomassie blue staining and fluorescence visualization. The yield was typically ~50% of the starting material. The concentration of the labeled protein was determined by the absorbance at 280 nm, after correcting for the absorbance due to the label (0.164 of that at 430 nm). The spectrum of the label was assumed to be the same as that determined for the adduct of MDCC with dithiothreitol.

Other fluorescent labels were attached in a similar way to PBP mutants, with minor modifications to the procedure, such as the ratio of label to the protein, reaction time, and pH.

Measurements Absorbance spectra were obtained on a Beckman DU70 spectrophotometer. Fluorescence measurements were obtained on a Farrand Mkl or a SLM 8000 photon counting spectrofluorimeter. Stopped flow experiments were carried out in a HiTech PQ/SF-53 apparatus, with a mercury lamp and HiTech IS-2 software.

The K$^+$-ATPase of subfragment 1 was measured using the spectrophotometric method of Webb (1992a) . The solution contained; 50 mM Tris.HCl pH 7.6, 0.6M KCl, 5mM EDTA, 5 mM ATP, 200 µM MESG (2-amino-6-mercapto-7-methylpurine ribonucleoside) and 12.5 unit-ml$^{-1}$ purine nucleoside phosphorylase. The absorbance was followed at 360 nm and the reaction was initiated by addition of ~0.5 µM subfragment 1. For proton release, the solution contained 0.6M KCl, 5 nM ATP and 10 mM EDTA pH 8.0. 5 mM KOH was titrated to maintain this pH.

The dissociation constant of the PBP.P$_i$ complex was determined using a modified version of an assay described by Pearlman et al (1969). The following were incubated for 30 min at room temperature in 0.5 mL 10 mM Tris.HCl, pH 8.0, using end-over-end stirring: 1 µM [$^{32}$P]P$_i$ (prefiltered through a 0.45 µm cellulose acetate filter to remove any particulate radioactivity) 0–30 µM PBP, 50 mg Sephadex G25 Superfine gel (Pharmacia), preswollen in a portion of the 0.5 mL buffer. The mixer was centrifuged and the radioactivity in the supernatant measured by scintillation counting. The P$_i$ partitions between the gel, the solution and PBP.P$_i$ complex. The PBP remains excluded from the gel. The data were fitted to the following equations using Grafit software (Leatherbarrow, 1992).

c.p.m. at [PBP]=c.p.m.$_0$ V$_t$((P-E$_p$)/V$_t$+E/V$_o$)/P where

E$_p$=(B-√(B$^2$-4PE))/2

B=P+E+KV$_t$ c.p.m.$_0$=c.p.m. at [PBP]=0

P=nmole of P$_i$

E=nmoles of PBP

V$_t$=total volume of solution

V$_o$=volume of solution occluded from gel (unknown)

K=dissociation constant (unknown)

The fluorescence titrations of P$_i$ with CPM-PBP (and MDCC-PBP) were fitted to the following equations using Enzfitter software:

Ratio of fluorescence at a given [P$_i$] to that at zero P$_i$=(Q[E$_p$]+[E]−[E$_p$])/[E] where

[E ]P=([P]+[E]+K−√(([P]+[E]+K)$^2$−4[P][E]))/2

[P]=concentration of P$_i$

[E]=concentration of CPM-PBP

Q=ratio of fluorescence for CPM-PBP.P$_i$ to that for the unliganded CPM-PBP

EXAMPLE 1

SYNTHESIS OF CPM-PBP AND MDCC-PBP

PBP was purified from the periplasm of E. coli strain ANCC75, overexpressing phos in a multicopy plasmid (Morita et al., 1983). A 4-liter culture gave 400–600 mg of PBP with a purity greater than 95% by polyacrylamide gel electrophoresis. The wild-type protein contains no cysteines and so fluorescent groups were attached initially via amines or carboxyls. All attempts to label the wild-type protein with a fluorophore gave at best a 15% fluorescence change on $P_i$ binding, about the same as that observed for the intrinsic tryptophan fluorescence. This is possibly due to relatively non-specific and multiple labeling To ensure that a single label could be attached, mutant PBP proteins were obtained by replacing single residues by cysteine, using oligonucleotide directed mutagenesis. The positions were chosen such that the residues were at the edge of the $P_i$-binding cleft described by Luecke & Quiocho (1990). These would be expected to experience a significant change in environment on $P_i$ binding, although the structure is known only for the $P_i$-bound form of PBP. In addition, the mutated residues were not directly involved in $P_i$ binding as elucidated by Luecke & Quiocho (1990). The cysteine mutants were labeled with a variety of fluorophores and these data are summarized in Table 1. One combination of mutant (A1297C) and fluorophore (MDCC; FIG. 1) gave a large fluorescence change with $P_i$, although several closely related fluorophores, including CPM and DACM, gave much smaller, changes. Most other labeled mutants were not tested to determine whether the lack of $P_i$ sensitivity is because they lacked $P_i$ binding, or because the fluorophore is insensitive to the putative conformation change. Serine 139 is involved in $P_i$ binding (Luecke & Quiocho, 1990), so the labeled S139C mutant PBP might be expected to be deficient in $P_i$ binding: this labeled mutant was therefore used as a null control. The A197C mutant was overproduced to the same extent as wild-type protein, so large amounts of the labeled protein could be obtained.

TABLE 1

Fluorescent group labelling of PBP mutants: the percent increase in fluorescence on adding $P_i$.

| Fluorophore | A9C | A57C | S139C | G140C | A197C | D292C |
|---|---|---|---|---|---|---|
| | | | | % | | |
| Acrylodan | 10 | −3 | −15 | 0 | 0 | 19 |
| MDCC | (a) | (a) | 0(d) | (a) | 405(d) | −2 |
| CPM | 15 | −4 | 0(d) | −10 | 65(d) | −6 |
| DACM | (a) | (a) | 10 | (a) | 34(d) | 0 |
| Dansyl aziridine | 20(c) | (a) | (b) | 0 | (b) | 4(c) |
| DEM | 0(c) | (a) | 0 | 0 | (b) | (a) |
| MIANS | (a) | (a) | (a) | (a) | 20 | 21(e) |

The conditions for measurement of fluorescence were ~5 µM labelled PBP in 10 mM Tris.HCl pH 8.0, to which 50 µM $P_i$ was added. Excitation and emission were at the maximum wavelength. DEM is N-2-[(1-maleimidyl) ethyl]-5-dimethylaminonaphthalenesulfonamide, MIANS is 2-[4'-(1-maleimidyl)anilino]naphthalene-6-sulfonic acid and DACM is 7-dimethylamino-3-(1-maleimidyl)-4-methylcoumarin. Amino acids are numbered from the N-terminus of the mature protein.
(a) Not determined.
(b) Negligible labelling.
(c) Very poor labelling.
(d) Labelled protein was purified on Q Sepharose resin as described in the Experimental procedures.
(e) Using the $P_i$ mop, the fluorescence change was 65%.

EXAMPLE 2

MDCC-PBP

Figure 2:
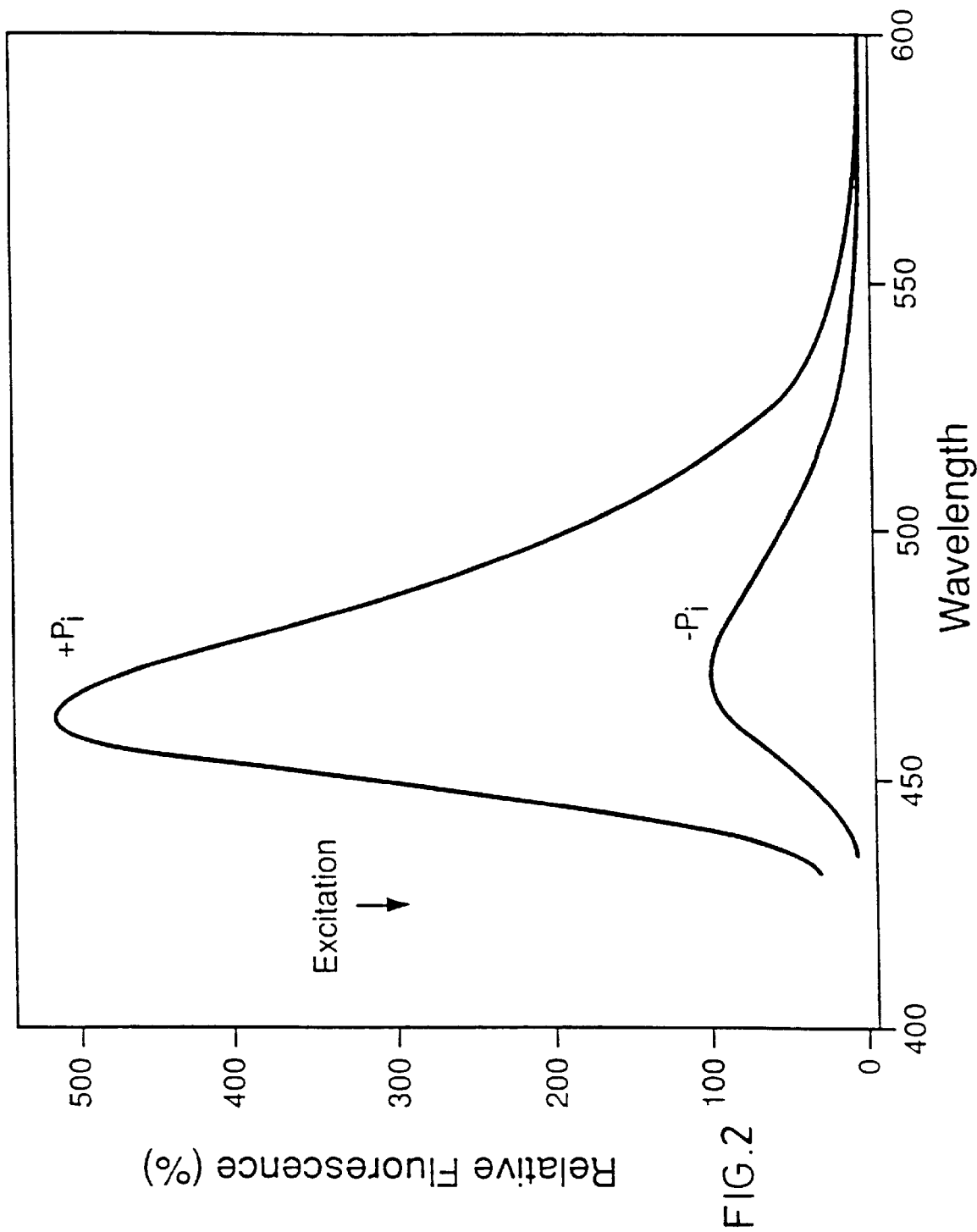
FIG. 2 shows the fluorescence emission spectra of MDCC-PBP in the presence and absence of $P_i$. 3.2 $\mu$M MDCC-PBP was in 10 mM PIPES, 1 mM $MgCl_2$ (pH 7.0) at 22° C. $P_i$ was added to 50 $\mu$M.

The $P_i$-sensitive labeled mutant, MDCC-PBP was purified further and tested as described in the Experimental Procedures to show it was a singly-labeled protein with no unlabeled protein or unbound fluorophore. The further purification is important as the unlabeled protein will also bind $P_i$. Unbound fluorophore would reduce the percentage fluorescence change by increasing the background and it might also slowly react with or bind to other components in the experimental system. The ion exchange chromatography separated MDCC-PBP completely from unlabeled PBP and unbound fluorophore. Thus the final labeled protein has a ratio of absorbance maxima, 280/430 nm of 1.8. The fluorescence excitation maximum is 425 nm and the emission maximum is 474 nm and the fluorescence change with excess $P_i$ at pH 7.0 for the conditions in FIG. 2 is 5.3-fold with a shift of maximum emission to 464 nm. The labeled protein could be stored at ~80° C. and was stable on ice for at least 5 days.

Figure 3:
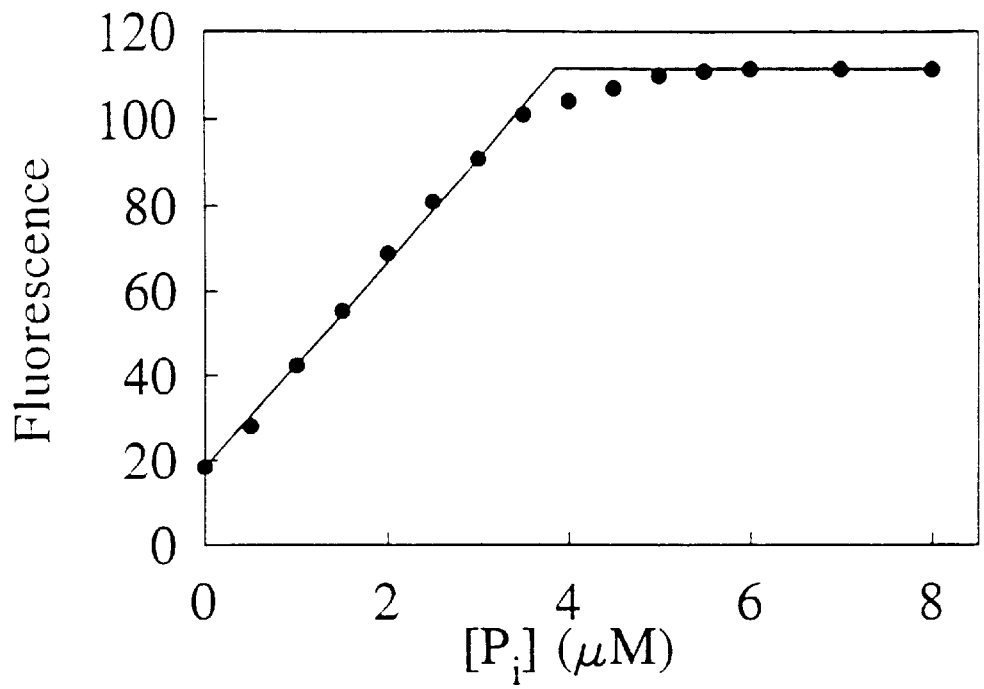
FIG. 3 shows the correlation between the fluorescence increase and $[P_i]$ added to the MDCC-PBP.

The product was characterized in several ways. Firstly it was important to show that the fluorescence responded linearly to $P_i$ and this is shown in FIG. 3, which suggests that the protein is 75–80% active, although some of the inactive protein may have $P_i$ bound, due to low concentrations of contaminating $P_i$, as discussed below The inactive protein does not bind added $P_i$ tightly. The dissociation constant was determined by titrating $P_i$ at low [MDCC-PBP] and measuring fluorescence (FIG. 4). This shows that binding is very tight, and the curve fits a dissociation constant of 0.03 MM at pH7.0 and a similar value was obtained at pH 8.0 (0.08 µM). A competition titration of MDCC-PBP.$P_i$, with wild-type PBP to give the relative affinities for $P_i$, showed the latter binds $P_i$ two-fold tighter than the labeled mutant. Because $P_i$ binding is very tight, these dissociation constants can be considered only approximate: the fluorescence titration could not be done at sufficiently low concentrations to obtain accurate values of $K_d$.

Because very small levels of $P_i$ contamination can affect the observed change on adding $P_i$ and because of variability in the protein activity, the maximum percent increase of fluorescence varies from 400–500%0 Although PBP is very specific for $P_i$ (Luecke & Quiocho, 1990), it was to be used as a probe in the presence of other phosphate species, such as esters or purine nucleotides and so it was important to know at what levels these might interfere with $P_i$ measurements. Several $P_i$ analogues were also tested (Table 2) and only arsenate and vanadate produced significant increases. For a titration of arsenate in a solution of MDCC-PBP, the fluorescence change was used to obtain a dissociation constant of 3 µM. In all cases except arsenate, when subsequently $P_i$ was added, the full fluorescent change was observed. The $P_i$ dependent fluorescence change was measured for a variety of conditions at a single concentration of $P_i$ (Table 2). The change is only slightly affected by pH (7–8) or ionic strength.

TABLE 2

Fluorescence change to MDCC-PBP due to various additions and solution compositions.

|  | % fluorescence increase |
|---|---|
| A. Additions | |
| $P_i$ (50 $\mu$M) | 430 |
| Pyrophosphate (100 $\mu$M) [a] | 6 |
| ATP (100 $\mu$M) [a,b] | 2 |
| ATP (1 mM) [a,b] | 11 |
| GDP (100 $\mu$M) [a] | 3 |
| ADP (100 $\mu$M) [a] | 3 |
| NPE-caged ATP (5 mM) [a,b,d] | 0 |
| Glucose-6-phosphate (100 $\mu$M) [a] | 3 |
| Sodium sulphate (1 mM) | 3 |
| $BeCl_2$ (100 $\mu$M)/NaF (100 mM) | 3 |
| $AlCl_3$ (100 $\mu$M)/NaF (100 mM) | 3 |
| Sodium arsenate (100 $\mu$M) | 313 |
| Sodium vanadate (100 $\mu$M) | 35 |
| B. Solution composition | |
| 10 mM Tris-HCl (pH 8.0) | 405 |
| 10 mM PIPES (pH 7.0) | 430 |
| 10 mM PIPES (pH 7.0), 1M NaCl [c] | 350 |

The solutions contained 2 $\mu$M MDCC-PBP (except for [b] 10 $\mu$M and [c] 3.2 $\mu$M) in 20 mM PIPES (pH 7.0) except where indicated. The solutions in B had 100 $\mu$M $P_i$ added to produce the indicated fluorescence change. The fluorescence change was measured at 465 nm with excitation at 425 nm. After the additions in A, addition of excess $P_i$ induced the full fluorescence increase.
[a] The solution was preincubated with the $P_i$ mop.
[d] NPE-caged ATP is $P^3$-1-(2-nitrophenyl)ethyl ATP.

Because MDCC-PBP binds $P_i$ tightly, it was important to consider the effect of $P_i$ contamination. Even in the absence of added phosphate compounds, it can be difficult to reduce $P_i$ contamination below 1 $\mu$m as $P_i$ is a fairly ubiquitous contaminant in buffers as well as biological solutions. Purine nucleotides inevitably have low concentrations of $P_i$ present due to hydrolysis. Proteins can also be contaminated, for example, actin has nucleotide bound and tests showed levels of $P_i$ approximately equimolar with the protein. $P_i$ is also a contaminant that binds to and washes off glassware. While some contaminants can be removed physically, such as by chromatography, it is not feasible to do this completely or simply. Because the $P_i$ probe is not enzymic, once all sites on the MDCC-PBP are bound by $P_i$, additional $P_i$ does not give a further signal. We therefore made use of a "phosphate mop", an enzymic back-up system to remove $P_i$, that consisted of 7-methyl guanosine (MEG) and purine nucleoside phosphorylase. This reaction was characterized as described for the thio analogue, MESG (Webb, 1992a). Using the absorbance change at 260 nm to monitor the rate of phosphorolysis, the $K_m$ is 59 $\mu$M for MEG, and 34 MM for $P_i$ and $k_{cat}$=109 s$^{-1}$ (pH 8.0, 20 mM Tris.HCl, 1 $\mu$M MgCl$_2$, 30° C.). The phosphorolysis is essentially irreversible, and all $P_i$ reacts chemically to form ribose 1-phosphate so that it is no longer available to bind to PBP: tests showed that $P_i$ could be reduced below ~0.1 $\mu$M. For experiments with the PBP, conditions were chosen such that the enzyme was present at low concentrations, insufficient to compete with the MDCC-PBP for the initial binding of $P_i$ released by the actomyosin, or other system, but sufficient to slowly remove $P_i$. This is illustrated in FIG. 5. Additions of $P_i$ show the rapid fluorescence increase on binding to the MDCC-PBP. The $P_i$ is slowly removed from the protein by the enzymic $P_i$ mop, and fluorescence returns to baseline: this process can be repeated several times, although there is a slight rise in baseline each time. This may represent a low residual $P_i$ or the effect of ribose 1-phosphate binding to MDCC-PBP.

In order to use the probe to measure $P_i$ release from ATPases and GTPases in real time it was important to know the kinetics of $P_i$ interaction with the labeled protein. These were measured in a stopped-flow apparatus and data for $P_i$ binding at pH 7.0 are shown in FIG. 6A. Because of the fast rates only part of the exponential is observed: a significant proportion of the reaction occurs during the dead time of the instrument (i.e. the time taken for the solution to flow between mixing and the observation chamber). The rates increased with [$P_i$], and there is saturation of rates at high $P_i$, although it is not clear if this saturation is due to the limitations of the stopped flow instrument, or whether there is a two step binding of $P_i$ and these data must therefore be treated with caution. The rates at [$P_i$]<5$\mu$M increase fairly linearly with [$P_i$], and so fit a simple one step binding model with the observed rate constant=$k_+$[$P_i$]+K. This fit gives $k_+$=136×10$^6$M$^{-1}$s$^{-1}$ and $k_-$=43 s$^{-1}$, although the latter value is particularly prone to error, for example due to $P_i$ contamination.

The dissociation rate of the MDCC-PBP.$P_i$ complex was measured directly in the stopped flow apparatus by rapid mixing of this complex with excess wild-type PBP. $P_i$ is released from the fluorescent complex and binds to the wild-type protein with a rate constant limited by the rate of release (FIG. 6B). The observed rate was 21.3±0.1 (S.E.M.) s$^{-1}$ (22° C., 10 $\mu$M PIPES, pH 7.0) for wild-type concentrations from 1.25 to 10 $\mu$M, with 0.25 $\mu$M MDCC-PBP and 0.125 $\mu$M $P_i$. Because this rate is constant over a range of wild-type concentrations and because the rate is much slower than that expected for $P_i$ binding, assuming the wild-type PBP has similar rate constant to the MDCC-PBP, the observed rate constant probably represents $P_i$ release. Using the value for the binding rate constant obtained above, $K_D$=$k_-$/$k_+$–0.15 $\mu$M, consistent with the value obtained by the titration, as the errors in the binding kinetic measurements are large and further work will be needed to clarify the mechanism of $P_i$ association.

Once it had been shown that $P_i$ binds rapidly to MDCC-PBP, this system was then used to measure the rate of $P_i$ release from actomyosin subfragment 1 ATPase. $P_i$ mop, MEG and the phosphorylase were present as outlined above. An initial experiment measured this rate for subfragment 1 in the absence of actin, and gave a single exponential increase in fluorescence with a rate constant of 0.09s$^{-1}$ (pH 7.0, 22° C.) (FIG. 7A) consistent with previous measurements (Trentham et al., 1972; Webb, 1992b). The end of the trace gives a further illustration of the effect of the $P_i$ mop, which slowly reduces the fluorescence The amount of mop added was selected so that it did not affect the observed rate of fluorescence rise due to the myosin-catalyzed ATP hydrolysis.

Two different experiments were done in the presence of actin. In the first [ATP] was similar to [subfragment 1], in the second [ATP] was high so that the reaction was clearly multiple turnover. The aim was to see if there was any burst of $P_i$ release faster than steady state rate, or if $P_i$ release was at the same rate as the steady state rate. Results of the first type of experiment are shown in FIG. 7B, for a measurement at high [actin]. The stopped-flow traces show several phases. Initially, solution at high fluorescence in the measuring chamber is replaced by fresh, unreacted solution when the syringes start to move. There is then a period when the unreacted solution is flowing through the chamber and at a time nominally zero the flow stops. On most traces there was an initial small rapid increase in fluorescence that had a rate constant expected for free $P_i$ binding to MDCC-PBP. This usually represented less than 0.3 $\mu$M $P_i$, and is probably low residual $P_i$ contamination particularly from actin, but may represent the binding of ribose 1-phosphate (the product of the $P_i$ mop; see above). The next phase was a lag followed by a rise in fluorescence with a rate that depended on [actin]. This final rise fitted a single exponential, and FIG. 8 shows the saturation of these fitted exponential rates at high [actin]. The data fit a two step binding model with step 1 assumed to be much faster than step 2. For this $K_d=26.0$ $\mu$M and $K_{+2}=15.2s^{-1}$. Steady state ATPase measurements gave $K_M$, 25 $\mu$M for similar solution conditions.

To obtain a rate constant for steady state hydrolysis requires an assumption about the active myosin concentration. To get round this problem and to ensure that ATP binding does not contribute to rate limitation, experiments were done with a large excess of ATP, so that any initial burst of $P_i$ release would be observed before steady state hydrolysis The result of one such experiment is shown in FIG. 9. Experiments were done at 50 or 100 $\mu$M ATP, 40–45$\mu$M actin and 2 or 4 $\mu$M subgragment 1 (mixing chamber concentrations) at different temperatures: the pH of the PIPES buffer was not readjusted for temperature change.

In these experiments there was also a small, initial rapid burst of fluorescence increase, much less than one turnover of the subfragment 1. Experiments where the data collection was more rapid indicated that the rate was that due to free $P_i$ binding. Following this there was a lag then a linear rise in fluorescence. The fluorescence rise then slows, which probably represents the onset of MDCC-PBP saturation. The [Pi] scale on these traces is based on the total [MDCC-PBP] and the total fluorescence change observed at long times when the MDCC-PBP is saturated with $P_i$.

EXAMPLE 3

CPM-PBP

All the methods of characterization described above were also used for CPM-PBP. The fluorescence response to added $P_i$ was linear. Titrations gave a dissociation constant of 14 $\mu$M at both pH 7.0 and 8.0 with an enhancement of 105% at pH 8.0 (10 mM Tris HCl) and 63% at pH 7.0 (10 mM PIPES). The fluorescence enhancement was reduced by increasing ionic strength. $P_i$ binding is fast, $36\times10^6 M^{-1}s^{-1}$ at pH 70, 20° C., low ionic strength. Results of these measurements are shown in FIGS. 10 to 13. Experiments performed on actomyosin using the CPM-PBP gave similar results as shown in FIGS. 14 and 15.

Analysis of the effects of $P_i$ analogues and solution composition was performed as for MDCC-PBP. The results are shown in Table 3.

TABLE 3

Fluorescence change to CPM-PBP due to various additions and solution compositions.

| | % fluorescence increase |
|---|---|
| A. Additions | |
| $P_i$ (50 $\mu$M) | 65 |
| Pyrophosphate (100 $\mu$M) [a] | 5 |
| ATP (100 $\mu$M) | 5 |
| ATP (1 mM) | 13 |
| GDP (100 $\mu$M) | 5 |
| ADP (100 $\mu$M) | 4 |
| Glucose-6-phosphate (100 $\mu$M) | 4 |
| Sodium sulphate (1 mM) | 0 |
| BeCl$_2$ (50 $\mu$M)/NaF (50 mM) | −10 |
| Al$_2$SO$_4$ (50 $\mu$M)/NaF (50 mM) | −8 |
| Sodium arsenate (100 $\mu$M) | 25 |
| Sodium vanadate (100 $\mu$M) | −2 |
| Sodium vanadate (1.1 mM) | −11 |

TABLE 3-continued

Fluorescence change to CPM-PBP due to various additions and solution compositions.

| | % fluorescence increase |
|---|---|
| B. Solution composition | |
| 10 mM Tris-HCl (pH 8.0), 50 mM NaCl | 63 |
| 10 mM Tris-HCl (pH 8.0), 100 mM NaCl | 45 |
| 10 mM Tris-HCl (pH 8.0), 500 mM NaCl | 32 |
| 20 mM Tris-HCl (pH 8.0) | 69 |
| 20 mM Tris-HCl (pH 7.5) | 60 |
| 20 mM Tris-HCl (pH 7.0) | 44 |
| 20 mM PIPES (pH 7.0) | 37 |

The solutions contained 6 $\mu$M (A), 7 $\mu$M (B) CPM-PBP in 10 mM Tris.HCl (pH 8.0) except where indicated. The solutions in B had 100 $\mu$M $P_i$ added to produce the indicated fluorescence change. The fluorescence change was measured at maximum emission with excitation at 397 nm. After the additions in A, addition of $P_i$ induced the full fluorescence increase.
[a] 2 $\mu$M CPM-PBP.

The invention is described above by way of example only and modifications within the scope of the invention are possible.

REFERENCES

Atwell, G. J. and Denny, W. A, Synthesis, 1984, 1032.

Barker, P. L. Gendler, P. L. and Rappoport, H., J. Org. Chem., 1981, 46, 2455

Dente, L., Sollazzo, H., Baldari, C., Cesareni, G. and Cortese R. (1985) in *DNA Cloning*, Vol. I (Glover, D. M. ed) pp.101–107, IRL Press Ltd., Oxford Gibson, T. J. (1984) *Studies on the Epstein-Barr virus genome* [Ph.D. thesis], Camridge University, England.

Keller, O. and Rudinger, J., Helv. Chim. Acta, 1975, 58, 531

Kessler, R. J. Vaughan, D. A., Schali, C., Fanestil, D. D., (1986), Adv. Exp. Med. Biol., 208, p.83–92.

Leatherbarrow, R. J. (1992) *Grafit* version 3, Erithacus Software Ltd., Staines, U.K.

Lehrer, S. S. and Kerwar, G. (1972) *Biochemistry* 11, 1211–1217.

Lindberg, O. & Ernster, L. (1956) Determination of organic phosphorus compounds by phosphate analysis. *Meth. Biochem. Anal.* 3, 1–22.

Luecke, H. and Quiocho, F. A. (1990) *Nature* 347, 402–406.

Magota, K., Otsuji, N., Miki, T., Horiuchi, T., Tsunasawa, S., Kondo, J., Sakiyama, F., Amemura, M., Morita, T., Shinagawa, H. and Nakata, A. (1984) *J. Bacteriol.* 157, 909–917.

Medveczky, N. and Rosenberg, H. (1970) *Biochim. Biophys. Acta* 211, 158–168.

Morita, T., Amemura, M., Makino, K., Shinagawa, H., Magota, K., Otsuji, N. and Nakata, A. (1983) *Euro J. Biochem.* 230, 427–435.

Nakamaye, K. L. and Eckstein, F. (1986) *Nucl.Acids Res.* 14, 9679–9698.

Pearlman, W. H., Fong, I. F. F., and Tou, J. H. (1969) *J. Biol. Chem.* 244 1373–1380

Sambrook, J., Fritsch, E. F. and Maniatis, T. (1989) *Molecular cloning. A laboratory manual*, 2nd ed., Cold Spring Harbor Laboratory Press, Cold Spring Harbor.

Surin, B. P., Jans, D. A., Fimmel, A. L., Shaw, D. C., Cox, G. B. and Rosenberg, H. (1984) *J. Bacteriol* 157, 772–778

Taylor, J. N., Ott, J. and Eckstein, F. (1985) *Nucl. Acids Res* 13, 8765–8785.

Torriani, A., (1990), *Bioessays,* 12, p.371–376

Trentham, D. R., Bardsley, R. G., Eccleston, J. F. and Weeds, A. G. (1972) *Biochem. J.* 126, 635–644.

Van Veldhoven, P. P. and Mannaerts, G. P. (1987) Inorganic and organic phosphate measurements in the nanomolar range. *Anal Biochem* 161, 45–48.

Webb, M. R. (1992a) *Proc. Natl. Acad. Sci. U.S.A.* 39, 4884–4887.

Webb, M. R. (1992b) *Phil. Trans. R. Soc. Lond. B* 336, 19–24.

Weeds, A. G. and Taylor, R. S. (1975) *Nature* 257, 54–560

Willsky, G. R. and Malamy, N. H. (1976) *J. Bacteriol.* 127, 595–609.

Yanisch-Perron, C., Vieira, J. and Messing, J. (1985) *Gene* 33, 103–119.

We claim:

1. A method for measuring or detecting inorganic phosphate ion in a sample comprising the steps of:

reacting a sample with a phosphate-binding protein, said protein containing (i) an inorganic phosphate ion binding site and (ii) a detectable label that produces a signal whose amplitude changes detectably upon the binding of inorganic phosphate ion to the binding site, under conditions effective to allow binding of any phosphate in the sample to said binding site, measuring a change in said signal, and from said change, measuring or detecting a level of inorganic phosphate ion in the sample.

2. The method of claim 1, wherein said label is a fluorescent label.

3. The method of claim 2, wherein said label is N-[2-(1-maleimidyl)ethyl]7-diethylaminocoumarin-3-carboxamide (MDCC).

4. The method of claim 1, wherein said protein is an *E. coli* phoS phosphate binding protein containing an A197C substitution to which said detectable label is attached.

5. The method of claim 4, wherein said label is a fluorescent label.

6. The method of claim 5, wherein said label is N-[2-(1-maleimidyl)ethyl]7-diethylaminocoumarin-3-carboxamide (MDCC).

7. The method of claim 1, wherein said reacting is performed in the presence of a phosphate mop that sequesters phosphate ion from said protein after said measuring or detecting step is complete.

8. The method of claim 7, wherein said phosphate mop is a purine nucleoside phosphorylase.

9. A phosphate binding protein for measuring or detecting inorganic phosphate ion, said protein containing (i) an inorganic phosphate ion binding site and (ii) a detectable label that produces a signal whose amplitude changes detectably upon the binding of inorganic phosphate ion to the binding site, wherein said protein is an *E. coli* phoS phosphate binding protein containing an A197C substitution to which said label is attached.

10. The protein of claim 9, wherein said label is a fluorescent label.

11. A protein in accordance with claim 10, wherein said label is N-[2-(1-maleimidyl)ethyl] 7-diethylaminocoumarin-3-carboxamide (MDCC).

12. An *E. coli* phoS phosphate binding protein containing an A197C substitution.

* * * * *